US008603972B2

(12) United States Patent  
Lau et al.

(10) Patent No.: US 8,603,972 B2
(45) Date of Patent: Dec. 10, 2013

(54) EXTENDED GLP-1 COMPOUNDS

(75) Inventors: Jesper Lau, Farum (DK); Florencio Zaragoza Dorwald, Smorum (DK); Lauge Schaffer, Lyngby (DK); Thomas Kruse Hansen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 997 days.

(21) Appl. No.: 11/908,836

(22) PCT Filed: Mar. 20, 2006

(86) PCT No.: PCT/EP2006/060856
§ 371 (c)(1),
(2), (4) Date: Oct. 9, 2009

(87) PCT Pub. No.: WO2006/097538
PCT Pub. Date: Sep. 21, 2006

(65) Prior Publication Data
US 2008/0207507 A1 Aug. 28, 2008

Related U.S. Application Data

(60) Provisional application No. 60/664,402, filed on Mar. 23, 2005.

(30) Foreign Application Priority Data

Mar. 18, 2005 (EP) .................... 05102173

(51) Int. Cl.
*A61K 38/26* (2006.01)
*A61P 3/10* (2006.01)
*C07K 14/605* (2006.01)

(52) U.S. Cl.
USPC ........... 514/7.2; 514/6.9; 530/308; 530/389.2

(58) Field of Classification Search
None
See application file for complete search history.

(56) References Cited

U.S. PATENT DOCUMENTS

| | | | |
|---|---|---|---|
| 5,545,618 A | 8/1996 | Buckley et al. |
| 6,268,343 B1 | 7/2001 | Knudsen et al. |
| 6,528,486 B1 | 3/2003 | Larsen et al. |
| 2001/0011071 A1 | 8/2001 | Knudsen et al. |
| 2004/0001827 A1 | 1/2004 | Dennis |
| 2004/0053370 A1 | 3/2004 | Glaesner et al. |
| 2007/0203058 A1 | 8/2007 | Lau et al. |
| 2009/0156478 A1 | 6/2009 | Lau et al. |

FOREIGN PATENT DOCUMENTS

| | | |
|---|---|---|
| EP | 1329458 | 7/2003 |
| EP | 05102171.5 | 3/2005 |
| EP | 1704165 A1 | 9/2006 |
| JP | 2000-500505 A | 1/2000 |
| JP | 2002-504527 A | 2/2002 |
| JP | 2002-508162 A | 3/2002 |
| JP | 2003-505347 | 2/2003 |
| JP | 2004-528014 A | 9/2004 |
| JP | 2004-535442 A | 11/2004 |
| JP | 2010-116407 A | 5/2010 |
| RU | 2006107600 | 10/2007 |
| WO | 90/11296 | 10/1990 |
| WO | 91/11457 A1 | 8/1991 |
| WO | WO 96/29342 | 9/1996 |
| WO | WO9629342 | 9/1996 |
| WO | 98/08872 A1 | 3/1998 |
| WO | WO 98/08871 | 3/1998 |
| WO | WO9808871 | 3/1998 |
| WO | 99/43341 | 9/1999 |
| WO | 99/43361 A1 | 9/1999 |
| WO | 99/43705 A1 | 9/1999 |
| WO | 9943707 | 9/1999 |
| WO | WO 99/43708 | 9/1999 |
| WO | WO9943708 | 9/1999 |
| WO | WO 00/34331 | 6/2000 |
| WO | WO0034331 | 6/2000 |
| WO | WO 00/69911 | 11/2000 |
| WO | WO0069911 | 11/2000 |
| WO | 01/04156 | 1/2001 |
| WO | 0151071 | 7/2001 |
| WO | 0258725 | 1/2002 |
| WO | WO 02/46227 | 6/2002 |
| WO | WO0246227 | 6/2002 |
| WO | 02098446 A1 | 12/2002 |
| WO | WO 03/002136 | 1/2003 |
| WO | WO03002136 | 1/2003 |
| WO | 03/013573 A1 | 2/2003 |
| WO | 03/040309 A2 | 5/2003 |
| WO | 03/058203 A2 | 7/2003 |
| WO | 03/087139 A2 | 10/2003 |
| WO | 2004/065621 A1 | 8/2004 |
| WO | 2004/074315 A2 | 9/2004 |
| WO | 2004/093823 A2 | 11/2004 |
| WO | 2004/099246 A2 | 11/2004 |
| WO | 2005/014049 A2 | 2/2005 |
| WO | 2005/028516 A2 | 3/2005 |
| WO | WO 2005/027978 | 3/2005 |

(Continued)

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*

(Continued)

*Primary Examiner* — Julie Ha
*Assistant Examiner* — Li Ni Komatsu
(74) *Attorney, Agent, or Firm* — Richard W. Bork

(57) ABSTRACT

The invention relates to protracted GLP-1 compounds and therapeutic uses thereof.

25 Claims, No Drawings

(56) References Cited

FOREIGN PATENT DOCUMENTS

| WO | 2005/058958 A2 | 6/2005 | |
|---|---|---|---|
| WO | WO 2006005667 A2 * | 1/2006 | ............ A61K 47/48 |
| WO | 2006/037810 A2 | 4/2006 | |
| WO | 2006/097536 A2 | 9/2006 | |
| WO | 2006/097537 | 9/2006 | |
| WO | 2006/097538 A1 | 9/2006 | |

OTHER PUBLICATIONS

Definition of moiety, from http://dictionary.reference.com/browse/moiety, pp. 1-3. Accessed Aug. 26, 2010.*

Residue definition, from http://dictionary.reference.com/browse/residue, pp. 1-4. Accessed Jul. 13, 2009.*

Deacon, C F et al Diabetologia Dipeptidyl Peptidase IV Resistant Analouges of Glucagon-Like Peptide-1 Which Have Extended Metabolic Stability and Improved Biological Activity 1998 41-271-278.

Holz, G G et al Current Medicinal Chemistry Glucagon-Like Peptide-1 Synthetic Analogs: New Therapeutic Agents for Use in the Treatment of Diabetes Mellitus Oct. 22, 2003 2471-2483.

Jung-Guk Kim et al. Diabetes Development and Characterization of a Glucagon-Like Peptide 1-Albumin Conjugate/ The Ability to Activate the Glucagon-Lile Peptide 1 Receptor in Vivo 2003 52-751-759.

Kurtzhals, P et al Biochemical Journal Albumin Binding of Insulins Acylated With Fatty Acids: Characterization of the Ligand-Protein Interaction and Correlation Between Binding Affinity and Timig of the Insulin Effect in Vivo 1995 312 3 725-731.

Ostrovski Y M Ukrayins'kyi Biokhimichnyi Zhurnal Comparative Characteristics of the Hydrophobic Nature of Certain Proteins by Their Interaction With 2-P Toluidino 1975 47 6 701-707.

Picó, G Studia Biophysica Use of 1-Anilino-8-Naphthalene Sulfonate as a Reporter Molecule to Study the Bile Salts-Bovine Serum Albumin Binding 1990 136 1 21-26.

Sheffield, W P Current Drug Targets Cardiovascular & Haematological Disorders Modification of Clearance of Therapeutic and Potentially Therapeutic Proteins Jan. 1, 2001 1-22.

Zobel, K et al. Bioorganic & Medicinal Chemistry Letters Phosphate Ester Serum Albumin Affinity Tags Greatly Improve Peptide Half-Life in Vivo 2003 13-1513-1515.

Knudsen, L.B. et al., "Potent Derivative of Glucagon-Like Peptide-1 with Pharmacokinetic Properties Suitable for Once Daily Administration," Journal of Medicinal Chemistry (2000), vol. 43, pp. 1664-1669.

Inflammatory Bowel Disease from e-Medicine, pp. 1.24, Accessed Sep. 24, 2008.

Green, Brian D. et al Biological Chemistry. Degradation, Receptor Binding, Insulin . . . 2004 385 2 169-177.

Greenwald Journal of the Controlled Release PEG Drugs: An Overview 2001 74-159-171.

Ji, J. et al. Biomaterials Stearyl Poly (Ethylene Oxide) Grafted Surfaces for Preferential Adsorption of Albumin. 2001 22-3015-3023.

Knudsen, L.B. Journal of Medicinal Chemistry Glucagon-Like Peptide-1 . . . 2004 47-4128-4134.

Simonovsky et al. Journal of Biomaterials Science, Polymer Edition Poly(Ether Urethane)s Incorporating Long Alkyl Side-Chains With Terminal Carboxyl Groups as Fatty Acid Mimics: Synthesis, Structural Characterization and Protein Adsorption 2005 16 12 1463-1483.

Soltero and Ekwurlbe Innovations in Pharmaceutical Technology the Oral Delivery of Protein and Peptide Drugs. Jan. 2001—106-110.

Still, J. Gordon, Diabetes/Metabolism Research Reviews, Development of Oral Insulin: Progress and Current Status, 2002, vol. 18, Suppl 1, pp. S29-S37.

Veronese F. M Biomaterials Peptide and Protein Pegylation: A Review of Porblems and Solutions 2001 22 5 405-417.

Chuang et al., 2002, "Pharmaceutical Strategies Utilizing Recombinant Human Serum Albumin," Pharmaceutical Research 19(5):569-577.

Han, 2002, "Targeted Prodrug Design to Optimize Drug Delivery," AAPS Pharmsci 2(1):1-11.

Hodgson et al., 2004, "The Synthesis Of Peptides And Proteins Containing Non-Natural Amino Acids," Chemical Reviews 33(7):422-430.

Kim et al., 2003, "Development and Characterization of a Glucagon-Like Peptide 1-Albumin Conjugate," Diabetes 52:751-759.

Makino et al., 2005, "Semisynthesis Of Human Ghrelin: Condensation Of A Boc-Protected Recombinant Peptide With A Synthetic O-Acylated Fragment," Biopolymers 79(5):238-247.

Okada, 2001, "Synthesis Of Peptides By Solution Methods," Current Organic Chemistry 5(1):1-43.

Schinzel et al., 1991, "The Phosphate Recognition Site Of *Escherichia coli* Maltodextrin Phosphorylase," Federation Of European Biochemical Society Jul. 1991, 286(1, 2):125-128.

Wallace, 1995, "Peptide Ligation And Semisynthesis," Current Opinion In Biotechnology 6(4):403-410.

Watanabe et al., "Structure-Activity Relationships of Glucagon-Like Peptide-1 (7-36) Amide: Insulinotropic Activities in Perfused Rat Pancreases, and Receptor Binding and Cyclic AMP Production in RINm5F Cells," Journal of Endocrinology, 1994, vol. 140, pp. 45-52.

Small Bowel Syndrome from e-Medicine, pp. 1-12, Accessed Sep. 24, 2008.

Declaration of Per Franklin Nielsen, 2012.

Annual Report 2003 Novo Nordisk A/S.

Curry, Stephen, Plasma Albumin as a Fatty Acid Carrier, Advances in Molecular and Cell Biology, 2004, vol. 33, pp. 29-46.

Annual Report 2004, Novo Nordisk A/S.

Nauck et al., The Once-Weekly Human GLP-1 Analogue . . . , EASD, 2012, 49th Annual Meeting.

International Non-Rpoprietary Names . . . , 2003, vol. 17(2), pp. 115, 125.

Table of S.C. Half-Life(Mining) and Potency Data 2011.

* cited by examiner

SEQUENCE LISTING

<160> NUMBER OF SEQ ID NOS: 3

<210> SEQ ID NO 1
<211> LENGTH: 31
<212> TYPE: PRT
<213> ORGANISM: Homo sapiens

<400> SEQUENCE: 1

```
His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Gly
            20                  25                  30
```

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa in position 1 is L-histidine,
      imidazopropionyl, alpha-hydroxy-histidine, D-histidine, desamino-
      histidine, 2-amino-histidine, -hydroxy-histidine, homohistidine,
      N-alpha-acetyl-histidine, N-alpha-formyl-histidine,
<220> FEATURE:
<221> NAME/KEY: MISC_FEATURE
<222> LOCATION: (1)..(1)
<223> OTHER INFORMATION: Xaa in position 1 is also alpha-fluoromethyl-
      histidine, alpha-methyl-histidine,3-pyridylalanine, 2-
      pyridylalanine or 4-pyridylalanine
<220> FEATURE:
<221> NAME/KEY: MISC_FEATURE
<222> LOCATION: (2)..(2)
<223> OTHER INFORMATION: Xaa in position 2 is Ala, Gly, Val, Leu, Ile,
      Thr, Ser, Lys, Aib, (1-aminocyclopropyl) carboxylic acid, (1-
      aminocyclobutyl) carboxylic acid, (1-aminocyclopentyl) carboxylic
      acid, (1-aminocyclohexyl) carboxylic acid, (1-aminocycloheptyl)
<220> FEATURE:
<221> NAME/KEY: MISC_FEATURE
<222> LOCATION: (2)..(2)
<223> OTHER INFORMATION: Xaa in position 2 is also (1-aminocyclooctyl)
      carboxylic acid;
<220> FEATURE:
<221> NAME/KEY: MISC_FEATURE
<222> LOCATION: (10)..(10)
<223> OTHER INFORMATION: Xaa in position 10 is Val or Leu
<220> FEATURE:
<221> NAME/KEY: MISC_FEATURE
<222> LOCATION: (12)..(12)
<223> OTHER INFORMATION: Xaa in position 12 is Ser, Lys or Arg
<220> FEATURE:
<221> NAME/KEY: MISC_FEATURE
<222> LOCATION: (13)..(13)
<223> OTHER INFORMATION: Xaa in position 13 is Tyr or Gln
<220> FEATURE:
<221> NAME/KEY: MISC_FEATURE
<222> LOCATION: (14)..(14)
<223> OTHER INFORMATION: Xaa in position 14 is Leu or Met
<220> FEATURE:
<221> NAME/KEY: MISC_FEATURE
<222> LOCATION: (16)..(16)
<223> OTHER INFORMATION: Xaa in position 16 is Gly, Glu or Aib
<220> FEATURE:
<221> NAME/KEY: MISC_FEATURE
<222> LOCATION: (17)..(17)
<223> OTHER INFORMATION: Xaa in position 17 is Gln, Glu, Lys or Arg
<220> FEATURE:
<221> NAME/KEY: MISC_FEATURE
<222> LOCATION: (19)..(19)
<223> OTHER INFORMATION: Xaa in position 19 is Ala or Val
<220> FEATURE:
<221> NAME/KEY: MISC_FEATURE

```
<222> LOCATION: (20)..(20)
<223> OTHER INFORMATION: Xaa in position 20 is Lys, Glu or Arg
<220> FEATURE:
<221> NAME/KEY: MISC_FEATURE
<222> LOCATION: (21)..(21)
<223> OTHER INFORMATION: Xaa in position 21 is Glu or Leu
<220> FEATURE:
<221> NAME/KEY: MISC_FEATURE
<222> LOCATION: (24)..(24)
<223> OTHER INFORMATION: Xaa in position 24 is Ala, Glu or Arg
<220> FEATURE:
<221> NAME/KEY: MISC_FEATURE
<222> LOCATION: (27)..(27)
<223> OTHER INFORMATION: Xaa in position 27 is Val or Lys
<220> FEATURE:
<221> NAME/KEY: MISC_FEATURE
<222> LOCATION: (28)..(28)
<223> OTHER INFORMATION: Xaa in position 28 is Lys, Glu, Asn or Arg
<220> FEATURE:
<221> NAME/KEY: MISC_FEATURE
<222> LOCATION: (29)..(29)
<223> OTHER INFORMATION: Xaa in position 29 is Gly or Aib
<220> FEATURE:
<221> NAME/KEY: MISC_FEATURE
<222> LOCATION: (30)..(30)
<223> OTHER INFORMATION: Xaa in position 30 is Arg, Gly or Lys, or is
      absent
<220> FEATURE:
<221> NAME/KEY: MISC_FEATURE
<222> LOCATION: (31)..(31)
<223> OTHER INFORMATION: Xaa in position 31 is Gly, Ala, Glu, Pro, Lys,
      Asn or is absent

<400> SEQUENCE: 2

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa in position 1 is also 3-pyridylalanine, 2-
      pyridylalanine or 4-pyridylalanine
<220> FEATURE:
<221> NAME/KEY: MISC_FEATURE
<222> LOCATION: (1)..(1)
<223> OTHER INFORMATION: Xaa in position 1 is L-histidine, D-histidine,
      desamino-histidine, 2-amino-histidine, -hydroxy-histidine,
      homohistidine, N-alpha-acetyl-histidine,
      N-alpha-fluoromethyl-histidine, alpha-methyl-histidine,
<220> FEATURE:
<221> NAME/KEY: MISC_FEATURE
<222> LOCATION: (2)..(2)
<223> OTHER INFORMATION: Xaa in position 2 is Ala, Gly, Val, Leu, Ile,
      Lys, Aib, (1-aminocyclopropyl) carboxylic acid, (1-
      aminocyclobutyl) carboxylic acid, (1-aminocyclopentyl) carboxylic
      acid, (1-aminocyclohexyl) carboxylic acid, (1-aminocycloheptyl)
<220> FEATURE:
<221> NAME/KEY: MISC_FEATURE
<222> LOCATION: (2)..(2)
<223> OTHER INFORMATION: Xaa in position 2 is also (1-aminocyclooctyl)
      carboxylic acid
<220> FEATURE:
<221> NAME/KEY: MISC_FEATURE
<222> LOCATION: (10)..(10)
<223> OTHER INFORMATION: Xaa in position 10 is Val or Leu;
<220> FEATURE:
<221> NAME/KEY: MISC_FEATURE
<222> LOCATION: (12)..(12)
<223> OTHER INFORMATION: Xaa in position 12 is Ser, Lys or Arg
```

```
<220> FEATURE:
<221> NAME/KEY: MISC_FEATURE
<222> LOCATION: (13)..(13)
<223> OTHER INFORMATION: Xaa in position 13 is Tyr or Gln
<220> FEATURE:
<221> NAME/KEY: MISC_FEATURE
<222> LOCATION: (14)..(14)
<223> OTHER INFORMATION: Xaa in position 14 is Leu or Met
<220> FEATURE:
<221> NAME/KEY: MISC_FEATURE
<222> LOCATION: (16)..(16)
<223> OTHER INFORMATION: Xaa in position 16 is Gly, Glu or Aib
<220> FEATURE:
<221> NAME/KEY: MISC_FEATURE
<222> LOCATION: (17)..(17)
<223> OTHER INFORMATION: Xaa in position 17 is Gln, Glu, Lys or Arg
<220> FEATURE:
<221> NAME/KEY: MISC_FEATURE
<222> LOCATION: (19)..(19)
<223> OTHER INFORMATION: Xaa in position 19  is Ala or Val
<220> FEATURE:
<221> NAME/KEY: MISC_FEATURE
<222> LOCATION: (20)..(20)
<223> OTHER INFORMATION: Xaa in position 20 is Lys, Glu or Arg
<220> FEATURE:
<221> NAME/KEY: MISC_FEATURE
<222> LOCATION: (21)..(21)
<223> OTHER INFORMATION: Xaa in position 21 is Glu or Leu
<220> FEATURE:
<221> NAME/KEY: MISC_FEATURE
<222> LOCATION: (24)..(24)
<223> OTHER INFORMATION: Xaa in position 24 is Ala, Glu or Arg
<220> FEATURE:
<221> NAME/KEY: MISC_FEATURE
<222> LOCATION: (27)..(27)
<223> OTHER INFORMATION: Xaa in position 27 is Val or Lys
<220> FEATURE:
<221> NAME/KEY: MISC_FEATURE
<222> LOCATION: (28)..(28)
<223> OTHER INFORMATION: Xaa in position 28 is Lys, Glu, Asn or Arg
<220> FEATURE:
<221> NAME/KEY: MISC_FEATURE
<222> LOCATION: (29)..(29)
<223> OTHER INFORMATION: Xaa in position 29 is Gly or Aib
<220> FEATURE:
<221> NAME/KEY: MISC_FEATURE
<222> LOCATION: (30)..(30)
<223> OTHER INFORMATION: Xaa in position 30 is Arg, Gly or Lys, or is
     absent
<220> FEATURE:
<221> NAME/KEY: MISC_FEATURE
<222> LOCATION: (31)..(31)
<223> OTHER INFORMATION: Xaa in position 31 is Gly, Ala, Glu, Pro, Lys,
     or is absent

<400> SEQUENCE: 3

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa
            20                  25                  30
```

US 8,603,972 B2

EXTENDED GLP-1 COMPOUNDS

CROSS-REFERENCE TO RELATED APPLICATIONS

This application is a 35 U.S.C. §371 national stage application of International Patent Application PCT/EP2006/060856 (published as WO 2006/097538), filed Mar. 20, 2006, which claimed priority of European Patent Application 05102173.1, filed Mar. 18, 2005; this application further claims priority under 35 U.S.C. §119 of U.S. Provisional Application 60/664,402, filed Mar. 23, 2005.

FIELD OF THE INVENTION

This invention relates to the field of therapeutic peptides, i.e. to new protracted GLP-1 compounds.

BACKGROUND OF THE INVENTION

Human GLP-1 is a 37 amino acid residue peptide originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. GLP-1 stimulates insulin secretion in a glucose-dependant manner, stimulates insulin biosynthesis, promotes beta cell rescue, decreases glucagon secretion, gastric emptying and food intake. Human GLP-1 is hydrolysed to GLP-1 (7-37) and GLP-1 (7-36)-amide which are both insulinotropic peptides. A simple system is used to describe fragments and analogues of this peptide. Thus, for example, [Gly$^8$]GLP-1 (7-37) designates an analogue of GLP-1 (7-37) formally derived from GLP-1(7-37) by substituting the naturally occurring amino acid residue in position 8 (Ala) by Gly. Similarly, (N$^{\epsilon 34}$-tetradecanoyl)[Lys$^{34}$]GLP-1(7-37) designates GLP-1(7-37) wherein the ε-amino group of the Lys residue in position 34 has been tetradecanoylated.

In the last decade a number of peptides have been isolated from the venom of the Gila monster lizards (*Heloderma suspectum* and *Heloderma horridum*). Exendin-4 is a 39 amino acid residue peptide isolated from the venom of *Heloderma suspectum*, and this peptide shares 52% homology with GLP-1 (7-37) in the overlapping region. Exendin-4 is a potent GLP-1 receptor agonist which has been shown to stimulate insulin release and ensuing lowering of the blood glucose level when injected into dogs. The group of exendin-4(1-39), certain fragments thereof, analogs thereof and derivatives thereof, are potent insulinotropic agents.

A range of different approaches have been used for modifying the structure of glucagon-like peptide 1 (GLP-1) compounds in order to provide a longer duration of action in vivo.

WO 96/29342 discloses peptide hormone derivatives wherein the parent peptide hormone has been modified by introducing a lipophilic substituent in the C-terminal amino acid residue or in the N-terminal amino acid residue.

WO 98/08871 discloses GLP-1 derivatives wherein at least one amino acid residue of the parent peptide has a lipophilic substituent attached.

WO 99/43708 discloses GLP-1 (7-35) and GLP-1 (7-36) derivatives which have a lipophilic substituent attached to the C-terminal amino acid residue.

WO 00/34331 discloses acylated GLP-1 analogs.

WO 00/69911 discloses activated insulinotropic peptides to be injected into patients where they are supposed to react with blood components to form conjugates and thereby allegedly providing longer duration of action in vivo.

WO 02/46227 discloses GLP-1 and exendin-4 analogs fused to human serum albumin in order to extend in vivo half-life.

Many diabetes patients particularly in the type 2 diabetes segment are subject to so-called "needle-phobia", i.e. a substantial fear of injecting themselves. In the type 2 diabetes segment most patients are treated with oral hypoglycaemic agents, and since GLP-1 compounds are expected to be the first injectable product these patients will be administered, the fear of injections may become a serious obstacle for the widespread use of the clinically very promising GLP-1 compounds. Thus, there is a need to develop new GLP-1 compounds which can be administered less than once daily, e.g. once every second or third day preferably once weekly, while retaining an acceptable clinical profile.

SUMMARY OF THE INVENTION

The invention provides a GLP-1 analog having a modification of at least one non-proteogenic amino acid residue in positions 7 and/or 8 relative to the sequence GLP-1 (7-37) (SEQ ID No 1), which is acylated with a moiety to the lysine residue in position 37 or 38, and where said moiety comprises at least two acidic groups, wherein one acidic group is attached terminally. The invention provides a pharmaceutical composition comprising such GLP-1 analog.

The invention provides the use of such a GLP-1 analog for the manufacture of a medicament for the treatment of various diseases.

DESCRIPTION OF THE INVENTION

In the present specification, the following terms have the indicated meaning:

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteogenic amino acids are:

Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic amino acid is a moiety which can be incorporated into a peptide via peptide bonds but is not a proteogenic amino acid. Examples are γ-carboxyglutamate, ornithine, phosphoserine, the D-amino acids such as D-alanine and D-glutamine, Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-Histidine, the beta analogs of amino acids such as β-alanine etc. D-histidine, desamino-histidine, 2-amino-histidine, β-hydroxy-histidine, homohistidine, N'-acetyl-histidine, α-fluoromethyl-histidine, α-methyl-histidine, 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A simple system is often used to describe analogues: For example [Arg$^{34}$]GLP-1(7-37)Lys designates a GLP-1(7-37) analogue wherein the naturally occurring lysine at position 34 has been substituted with arginine and wherein a lysine has been added to the terminal amino acid residue, i.e. to the Gly$^{37}$. All amino acids for which the optical isomer is not stated is to be understood to mean the L-isomer. In embodiments of the invention a maximum of 17 amino acids have been modified. In embodiments of the invention a maximum of 15 amino acids have been modified. In embodiments of the invention a maximum of 10 amino acids have been modified. In embodiments of the invention a maximum of 8 amino acids have been modified. In embodiments of the invention a maximum of 7 amino acids have been modified. In embodiments of the invention a maximum of 6 amino acids have been modified. In embodiments of the invention a maximum of 5 amino acids have been modified. In embodiments of the invention a maximum of 4 amino acids have been modified. In embodiments of the invention a maximum of 3 amino acids have been modified. In embodiments of the invention a maximum of 2 amino acids have been modified. In embodiments of the invention 1 amino acid has been modified.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. An example of a derivative of GLP-1(7-37) is N$^{ε26}$-((4S)-4-(hexadecanoylamino)-carboxy-butanoyl)[Arg$^{34}$, Lys$^{26}$] GLP-1-(7-37).

The term "GLP-1 peptide" as used herein means GLP-1(7-37) (SEQ ID No 1), a GLP-1(7-37) analogue, a GLP-1(7-37) derivative or a derivative of a GLP-1(7-37) analogue. In one embodiment the GLP-1 peptide is an insulinotropic agent.

The term "insulinotropic agent" as used herein means a compound which is an agonist of the human GLP-1 receptor, i.e. a compound which stimulates the formation of cAMP in a suitable medium containing the human GLP-1 receptor (one such medium disclosed below). The potency of an insulinotropic agent is determined by calculating the EC$_{50}$ value from the dose-response curve as described below.

Baby hamster kidney (BHK) cells expressing the cloned human GLP-1 receptor (BHK-467-12A) were grown in DMEM media with the addition of 100 IU/mL penicillin, 100 μg/mL streptomycin, 5% fetal calf serum and 0.5 mg/mL Geneticin G-418 (Life Technologies). The cells were washed twice in phosphate buffered saline and harvested with Versene. Plasma membranes were prepared from the cells by homogenisation with an Ultraturrax in buffer 1 (20 mM HEPES-Na, 10 mM EDTA, pH 7.4). The homogenate was centrifuged at 48,000×g for 15 min at 4° C. The pellet was suspended by homogenization in buffer 2 (20 mM HEPES-Na, 0.1 mM EDTA, pH 7.4), then centrifuged at 48,000×g for 15 min at 4° C. The washing procedure was repeated one more time. The final pellet was suspended in buffer 2 and used immediately for assays or stored at −80° C.

The functional receptor assay was carried out by measuring cyclic AMP (cAMP) as a response to stimulation by the insulinotropic agent. cAMP formed was quantified by the AlphaScreen™ cAMP Kit (Perkin Elmer Life Sciences). Incubations were carried out in half-area 96-well microtiter plates in a total volume of 50 μL buffer 3 (50 mM Tris-HCl, 5 mM HEPES, 10 mM MgCl$_2$, pH 7.4) and with the following additions: 1 mM ATP, 1 μM GTP, 0.5 mM 3-isobutyl-1-methylxanthine (IBMX), 0.01% Tween-20, 0.1% BSA, 6 μg membrane preparation, 15 μg/mL acceptor beads, 20 μg/mL donor beads preincubated with 6 nM biotinyl-cAMP. Compounds to be tested for agonist activity were dissolved and diluted in buffer 3. GTP was freshly prepared for each experiment. The plate was incubated in the dark with slow agitation for three hours at room temperature followed by counting in the Fusion™ instrument (Perkin Elmer Life Sciences). Concentration-response curves were plotted for the individual compounds and EC$_{50}$ values estimated using a four-parameter logistic model with Prism v. 4.0 (GraphPad, Carlsbad, Calif.).

The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV. In one embodiment a DPP-IV protected peptide is more resistant to DPP-IV than GLP-1(7-37) or Exendin-4(1-39). Resistance of a peptide to degradation by dipeptidyl aminopeptidase IV is determined by the following degradation assay:

Aliquots of the peptide (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

The term "C$_{1-6}$-alkyl" as used herein means a saturated, branched, straight or cyclic hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl, cyclohexane and the like. The term "pharmaceutically acceptable" as used herein means suited for normal pharmaceutical applications, i.e. giving rise to no adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

In another aspect the present invention relates to an acylated GLP-1 analogue that can bind to albumin and the GLP-1 receptor simultaneously.

In another aspect the present invention relates to an acylated GLP-1 analogue that bind to the GLP-1 receptor with an affinity below 100 nM, preferable below 30 nM in the presence of 2% albumin.

In another aspect the present invention relates to an acylated GLP-1 analogue which affinity to the GLP-1 receptor is only partly decreased when comparing the affinity in the presence of very low concentration (e.g. 0.005% to 0.2%) of human albumin to the affinity in the presence of 2% human albumin. The shift in binding affinity under these conditions is less than 50 fold, preferable below 30 fold and more preferable below 10 fold.

The term "albumin binding moiety" as used herein means a residue which binds non-covalently to human serum albumin. The albumin binding residue attached to the therapeutic polypeptide typically has an affinity below 10 µM to human serum albumin and preferably below 1 µM. A range of albumin binding residues are known among linear and branched lipophilic moieties containing 4-40 carbon atoms having a distal acidic group.

The term "hydrophilic linker" as used herein means a spacer that separates a peptide and an albumin binding residue with a chemical moiety which comprises at least 5 non-hydrogen atoms where 30-50% of these are either N or O.

The term "acidic groups" as used herein means organic chemical groups which are fully or partly negatively charged at physiological pH. The pKa value of such groups is below 7, preferable below 5. This includes but is not limited to carboxylic acids, sulphonic acids, phosphoric acids or heterocyclic ring systems which are fully or partly negatively charged at physiological pH.

The present invention provides a GLP-1 analog, acylated with a lipophillic albumin binding moiety containing at least two free acidic chemical groups attached via a non natural amino acid linker to a lysine residue in position 37 or 38. In an embodiment of the invention the lysine is in position 38.

The present invention also provides an acylated GLP-1 analog where said GLP-1 analog is stabilised against DPP-IV by modification of at least one amino acid residue in positions 7 and 8 relative to the sequence GLP-1(7-37) (SEQ ID No 1), and where said acylation is a diacid attached to a lysine residue in position 37 or 38 optionally via a non natural amino acid hydrophilic linker. In an embodiment of the invention the lysine is in position 38.

The present invention also provides a method for increasing the time of action in a patient of a GLP-1 analog, characterised in acylating said GLP-1 analog with a diacid on the lysine residue in position 37 or 38 of said GLP-1 analog. In an embodiment of the invention the lysine is in position 38.

The present invention also provides a method for increasing the time of action in a patient of a GLP-1 analog to more than about 40 hours, characterised in modifying at least one of the amino acid residues in positions 7 and 8 of a GLP-1(7-37)Lys peptide or an analog thereof, and acylating the C-terminal amino acid Lys38 residue of the GLP-1 analog with a diacid via a hydrophillic spacer.

The present invention also provides pharmaceutical compositions comprising a compound according to the present invention and the use of compounds according to the present invention for preparing medicaments for treating disease.

In one embodiment of the invention said GLP-1 analog is Aib$^8$,Arg$^{26,34}$-GLP-1(7-37)Lys, Aib$^{8,22}$,Arg$^{26,34}$-GLP-1(7-37)Lys, or Gly$^8$,Arg$^{26,34}$GLP-1-(7-37)Lys.

In the below structural formula II the moiety U is a diradical may be attached to the terminal groups B and the amino group of the lysine amino acid in the peptide in two different ways. In embodiments of the invention the U in formula II is attached with the group B attached at the end of the alkyl chain and the peptide at the other end.

In the formulas below the terminal bonds from the attached groups are to be regarded as attachment bonds and not ending in methylene groups unless stated.

In the formulas below

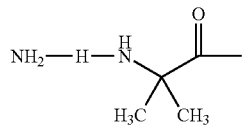

means the H$_2$N-His-Aib-N-terminal of the GLP-1 analogue.

In one aspect the present invention relates to a GLP-1 analog, acylated with a lipophillic albumin binding moiety containing at least two free acidic chemical groups attached via a non natural amino acid linker to a lysine residue in position 37 or 38. In an embodiment of the invention the lysine is in position 38.

In an embodiment, the term free acidic chemical groups is to be understood as having the same meaning as "acidic groups" as used herein.

In another aspect the present invention relates to an acylated GLP-1 analog where said GLP-1 analog is stabilised against DPP-IV by modification of at least one amino acid residue in positions 7 and 8 relative to the sequence GLP-1 (7-37) (SEQ ID No 1), and where said acylation is a diacid attached to a lysine residue in position 37 or 38 optionally via a non natural amino acid hydrophilic linker. In an embodiment of the invention the lysine is in position 38.

In an embodiment of the invention a GLP-1 analog having a modification of at least one non-proteogenic amino acid residue in positions 7 and/or 8 relative to the sequence GLP-1(7-37) (SEQ ID No 1), which is acylated with a moiety to the lysine residue in position 37 or 38, and where said moiety comprises at least two acidic groups, wherein one acidic group is attached terminally. In an embodiment of the invention the lysine is in position 38.

An embodiment provides a GLP-1 analog according to the above embodiment, wherein the moiety attached in position 37 or 38 comprises a hydrophilic linker. In an embodiment of the invention the lysine is in position 38.

An embodiment provides a GLP-1 analog according to the above embodiments, wherein the hydrophilic linker comprises at least 5 non-hydrogen atoms where 30-50% of these are either N or O.

An embodiment provides a GLP-1 analog according to any of the above embodiments, wherein the moiety attached in position 37 or 38 comprises an albumin binding moiety separated from the peptide by the hydrophilic linker. In an embodiment of the invention the lysine is in position 38.

An embodiment provides a GLP-1 analog according to the above embodiment, wherein the albumin binding moiety is a linear or branched lipophilic moiety containing 4-40 carbon atoms having a distal acidic group.

An embodiment provides a GLP-1 analog according to any of the above embodiments, wherein the acylated moiety is B—U', where U' is selected from

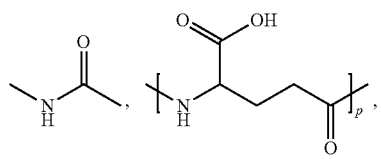

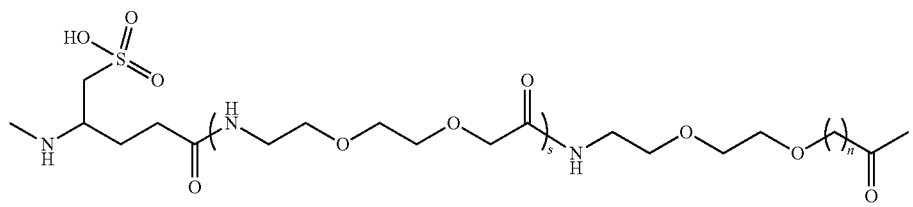

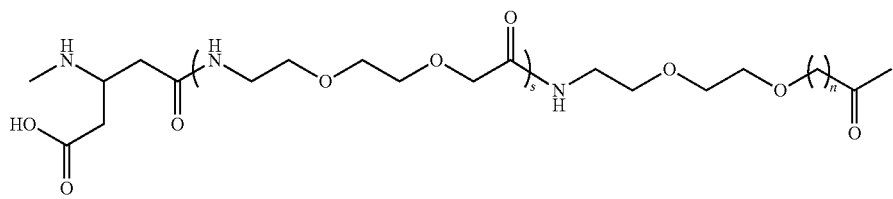

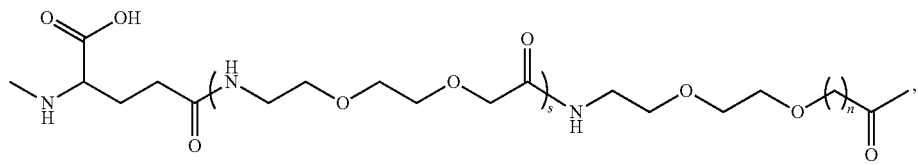

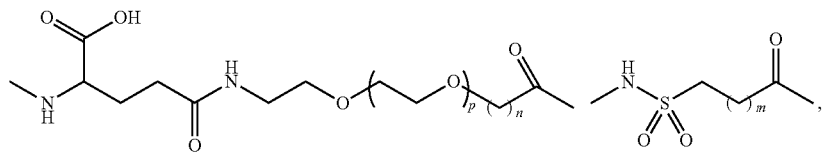

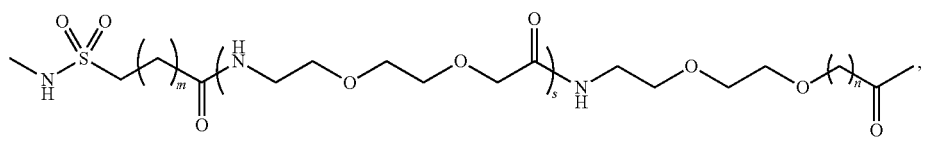

-continued

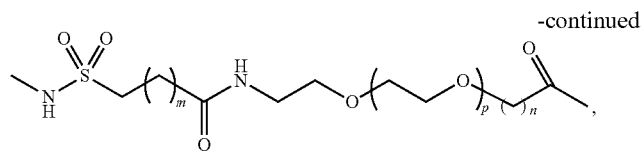

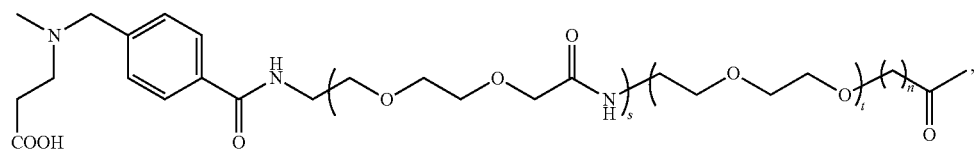

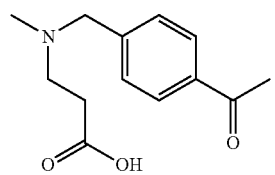

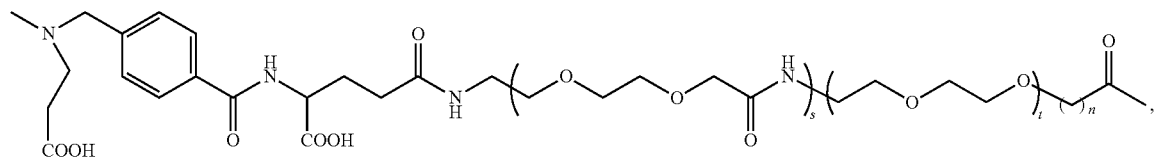

m is 0, 1, 2, 3, 4, 5, or 6,
n is 1, 2 or 3
s is 0, 1, 2, or 3,
t is 0, 1, 2, 3, or 4
p is 1, 2, 3, 4, 5, 6, 7, 8, 9, 10, 11, 12, 13, 14, 15, 16, 17, 18, 19, 20, 21, 22, or 23; and where B is an acidic group selected from

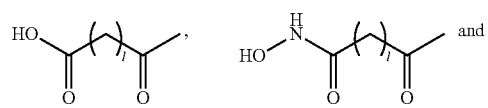 and

-continued

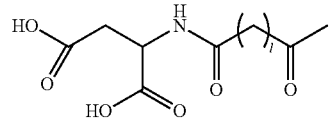

where l is 12, 13, 14, 15, 16, 17, 18, 19 or 20;

An embodiment provides a GLP-1 analog according to any of the above embodiments, which is a compound of formula I (SEQ ID No. 2):

Formula I

Xaa$_7$-Xaa$_8$-Glu-Gly-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Trp-Leu-Xaa$_{33}$-Xaa$_{34}$-Xaa$_{35}$-Xaa$_{36}$-Xaa$_{37}$ 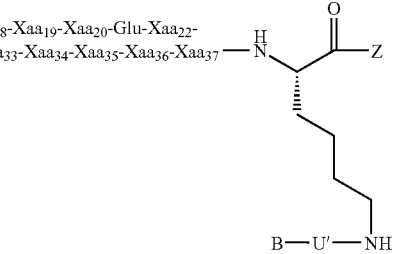

wherein

Xaa$_7$ is L-histidine, imidazopropionyl, α-hydroxy-histidine, D-histidine, desamino-histidine, 2-amino-histidine, β-hydroxy-histidine, homohistidine, N$^\alpha$-acetyl-histidine, N$^\alpha$-formyl-histidine, α-fluoromethyl-histidine, α-methyl-histidine, 3-pyridylalanine, 2-pyridylalanine or 4-pyridylalanine Xaa$_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly, Glu or Aib;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val or Lys;
Xaa$_{34}$ is Lys, Glu, Asn or Arg;
Xaa$_{35}$ is Gly or Aib;
Xaa$_{36}$ is Arg, Gly or Lys, or is absent;
Xaa$_{37}$ is Gly, Ala, Glu, Pro, Lys, Asn or is absent;

If Xaa$_{36}$ or Xaa$_{37}$ is absent, the C-terminal amino acid is lysine as stated in the formula above.

Z is OH or NH$_2$

U' is a spacer selected from

-continued

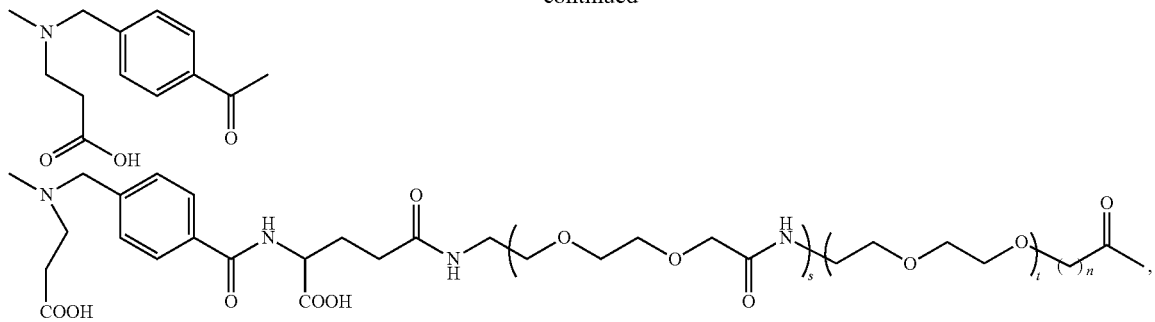

m is 0, 1, 2, 3, 4, 5, or 6,
n is 1, 2 or 3
s is 0, 1, 2, or 3,
t is 0, 1, 2, 3, or 4
p is 1, 2, 3, 4, 5, 6, 7, 8, 9, 10, 11, 12, 13, 14, 15, 16, 17, 18, 19, 20, 21, 22, or 23;
and where B is an acidic group selected from

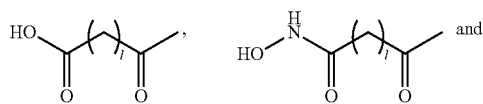

where l is 12, 13, 14, 15, 16, 17, 18, 19 or 20

In one embodiment of the invention said GLP-1 analog is $Aib^8,Arg^{26,34}$-GLP-1(7-37)Lys, $Aib^{8,22},Arg^{26,34}$-GLP-1(7-37)Lys, or $Gly^8,Arg^{26,34}$GLP-1-(7-37)Lys.

In another embodiment the invention relates to a compound of formula II (Seq. id. No. 3)

The formula II is identical to formula I as stated in an embodiment above, where the moiety B—U is replaced by B—U'. The difference being only the incorporation of the carboxy group in the U' relative to U, which is without the attaching carboxy group.

In formula II each of the Xaa's has the following meaning:
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{16}$ is Val or Leu;
$Xaa_{18}$ is Ser, Lys or Arg;
$Xaa_{19}$ is Tyr or Gln;
$Xaa_{20}$ is Leu or Met;
$Xaa_{22}$ is Gly, Glu or Aib;
$Xaa_{23}$ is Gln, Glu, Lys or Arg;
$Xaa_{25}$ is Ala or Val;
$Xaa_{26}$ is Lys, Glu or Arg;
$Xaa_{27}$ is Glu or Leu;
$Xaa_{30}$ is Ala, Glu or Arg;
$Xaa_{33}$ is Val or Lys;
$Xaa_{34}$ is Lys, Glu, Asn or Arg;
$Xaa_{35}$ is Gly or Aib;
$Xaa_{36}$ is Arg, Gly or Lys, or is absent;
$Xaa_{37}$ is Gly, Ala, Glu, Pro, Lys, or is absent;
Z is OH or $NH_2$
U is a spacer selected from Formula II $Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-Trp-Leu-$Xaa_{33}$-$Xaa_{34}$-$Xaa_{35}$-$Xaa_{36}$-$Xaa_{37}$—

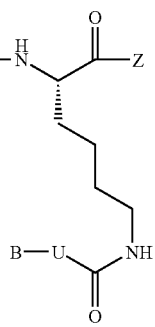

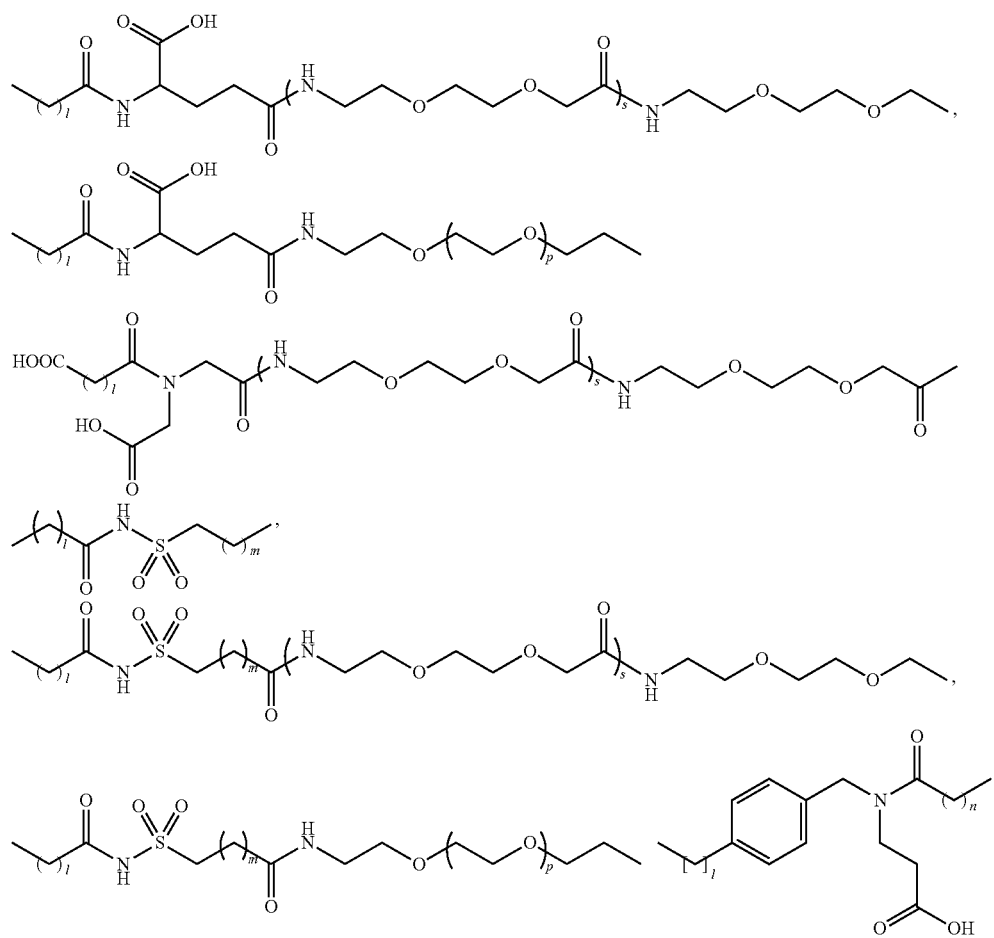
where n is 12, 13, 14, 15, 16, 17 or 18
l is 12, 13, 14, 15, 16, 17 or 18,
m is 0, 1, 2, 3, 4, 5, or 6,
s is 0, 1, 2, or 3,
p is 3, 4, 5, 6, 7, 8, 9, 10, 11, 12, 13, 14, 15, 16, 17, 18, 19, 20, 21, 22, or 23
B is an acidic group selected from
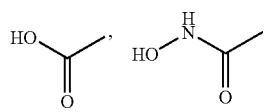
In another embodiment of the invention U is
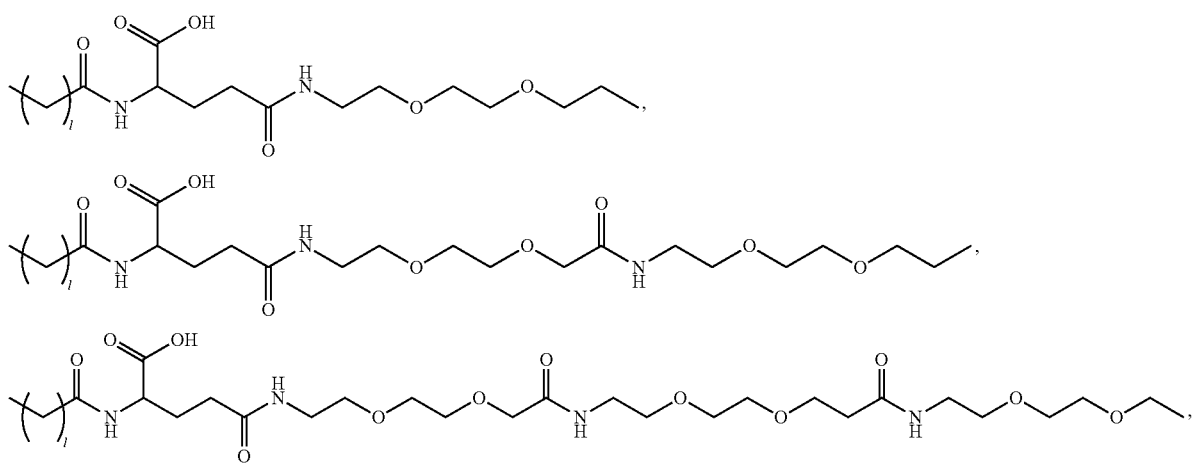

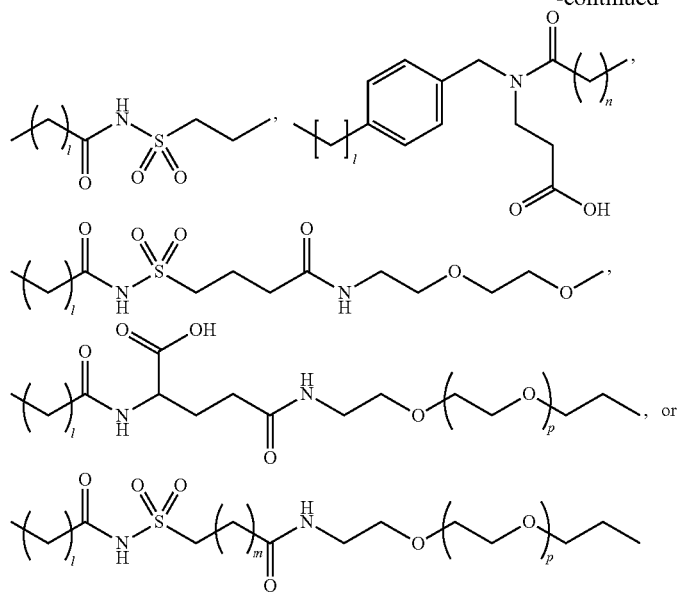
wherein l is 14, 15 or 16
n is 15, 16, 17 or 18,
p is 3, 7, 11 or 24
In the embodiments below when referring to U' in formula I it is to be understood as also referring to formula II and U, with the only difference being the carboxy group.
An embodiment provides a GLP-1 analog according to the embodiments above, wherein U' is selected from
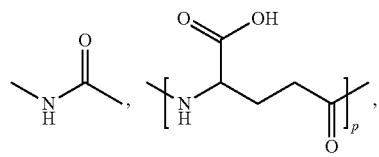
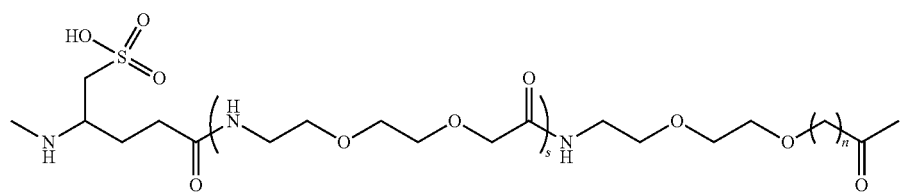
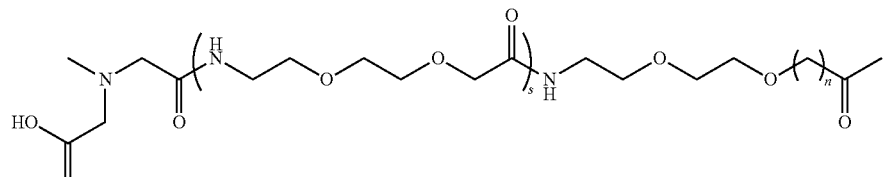
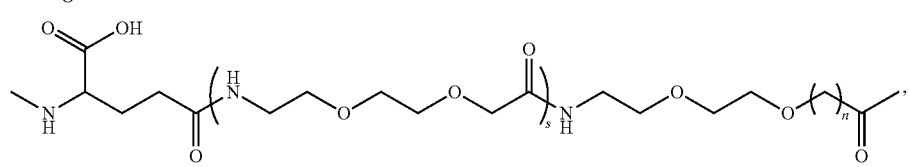

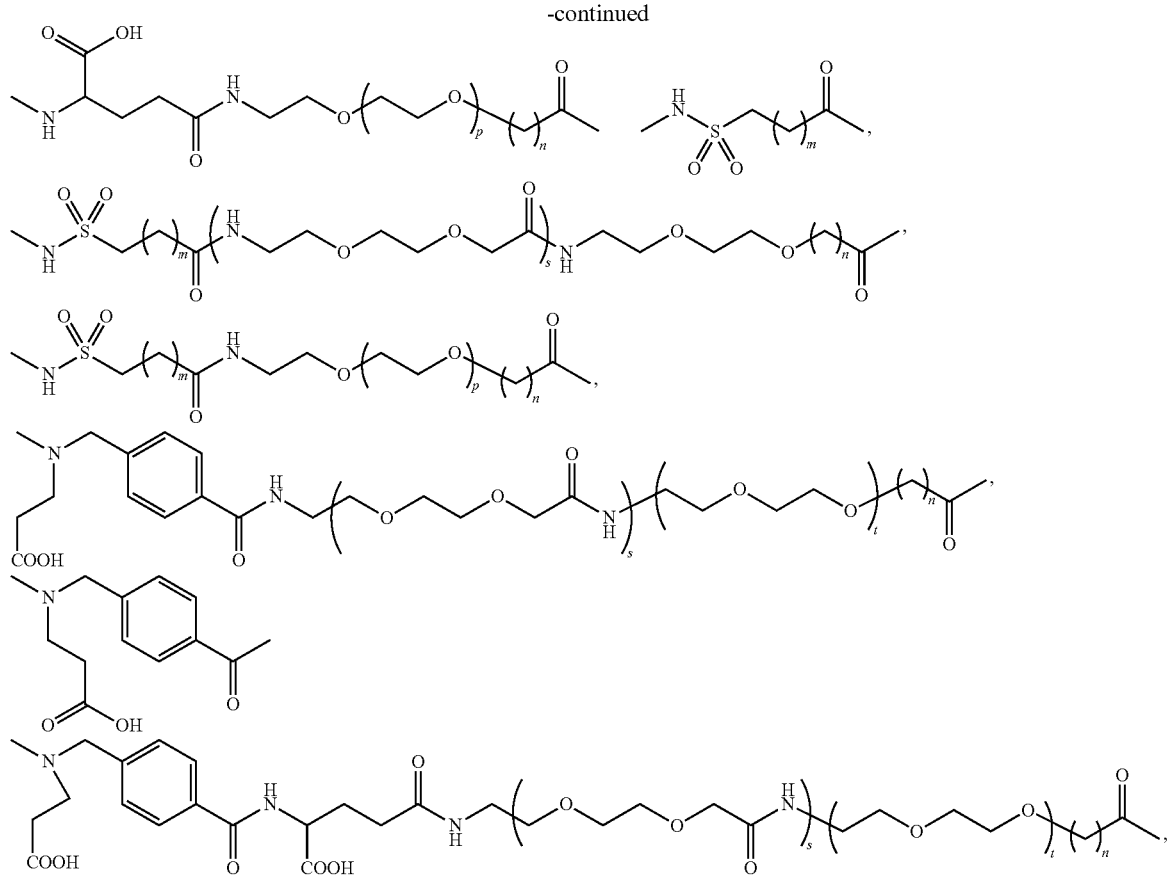
m is 2, 3, 4 or 5,
n is 1 or 2
s is 0, 1, or 2,
t is 0, 1, 2, or 3
p is 1, 2, 3, 4, 7, 11 or 23
An embodiment provides a GLP-1 analog according to the embodiments above, wherein B—U'— is
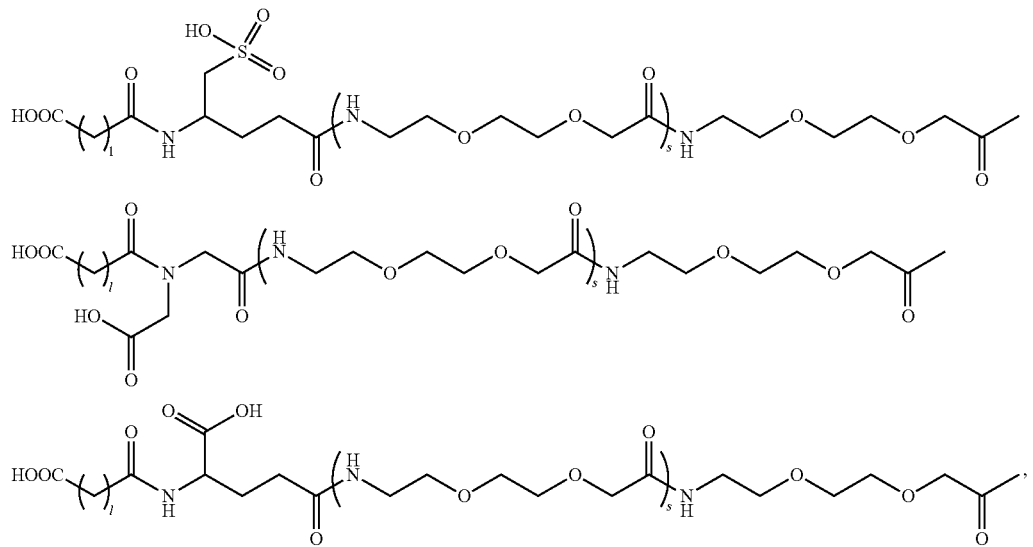

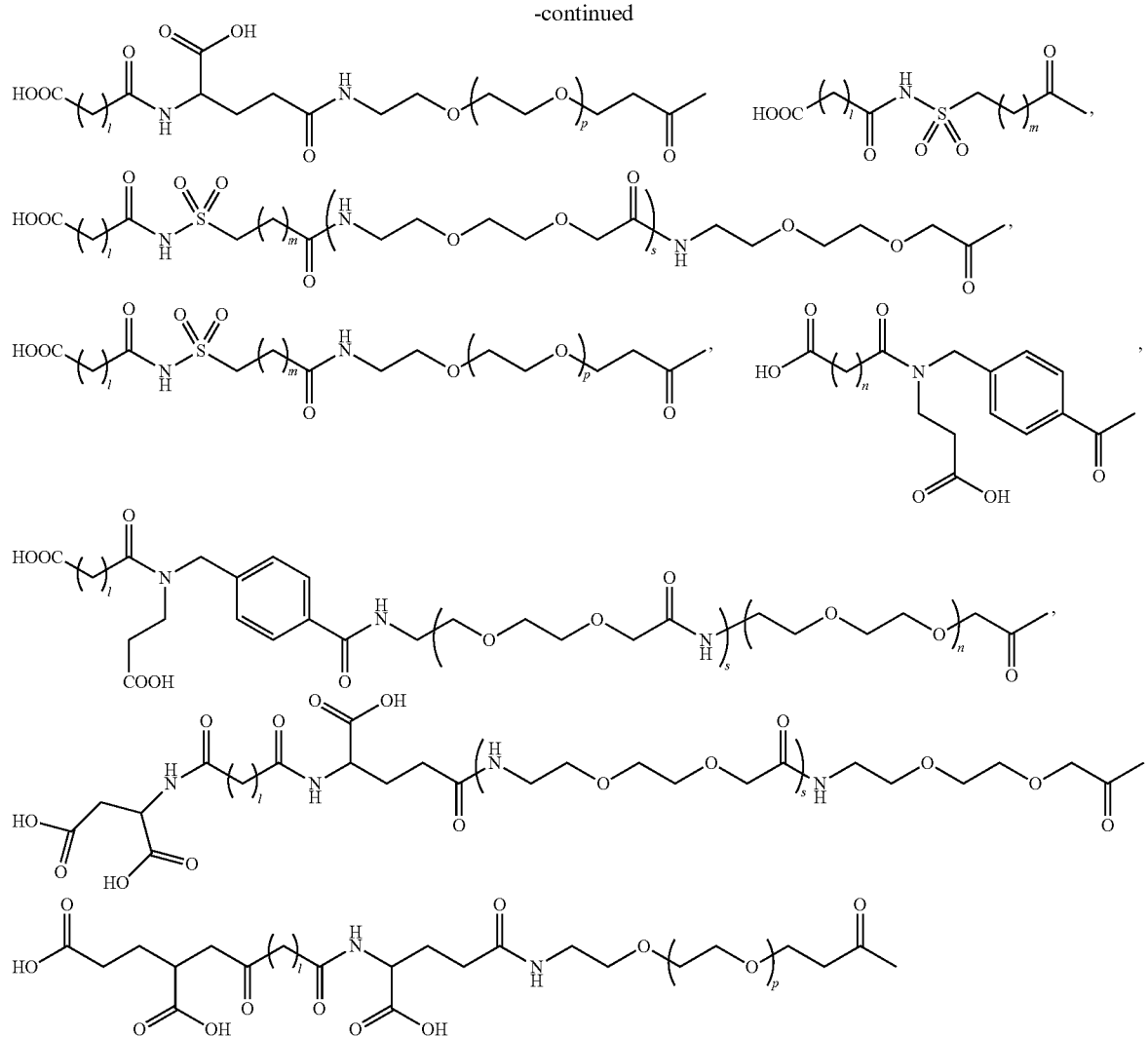
where l is 14, 15, 16, 17, 18, 19 or 20;
p is 1, 2, 3, 4, 7, 8, 9, 10, 11 or 12.
s is 0, 1 or 2
t is 0 or 1;
An embodiment according to the above wherein where l is 14, 15, 16, 17 or 18
p is 1, 2, 3, 4 or 11;
s is 0, 1 or 2;
t is 0 or 1;
An embodiment provides a GLP-1 analog according to the embodiment above, wherein B—U' is
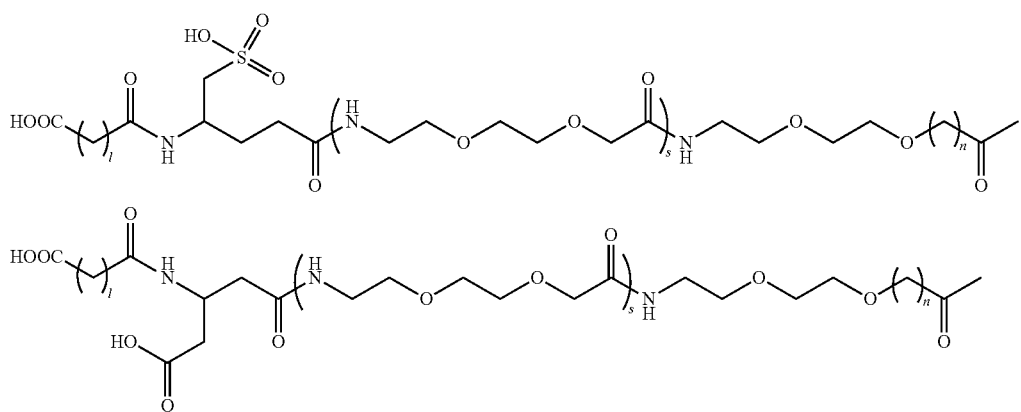

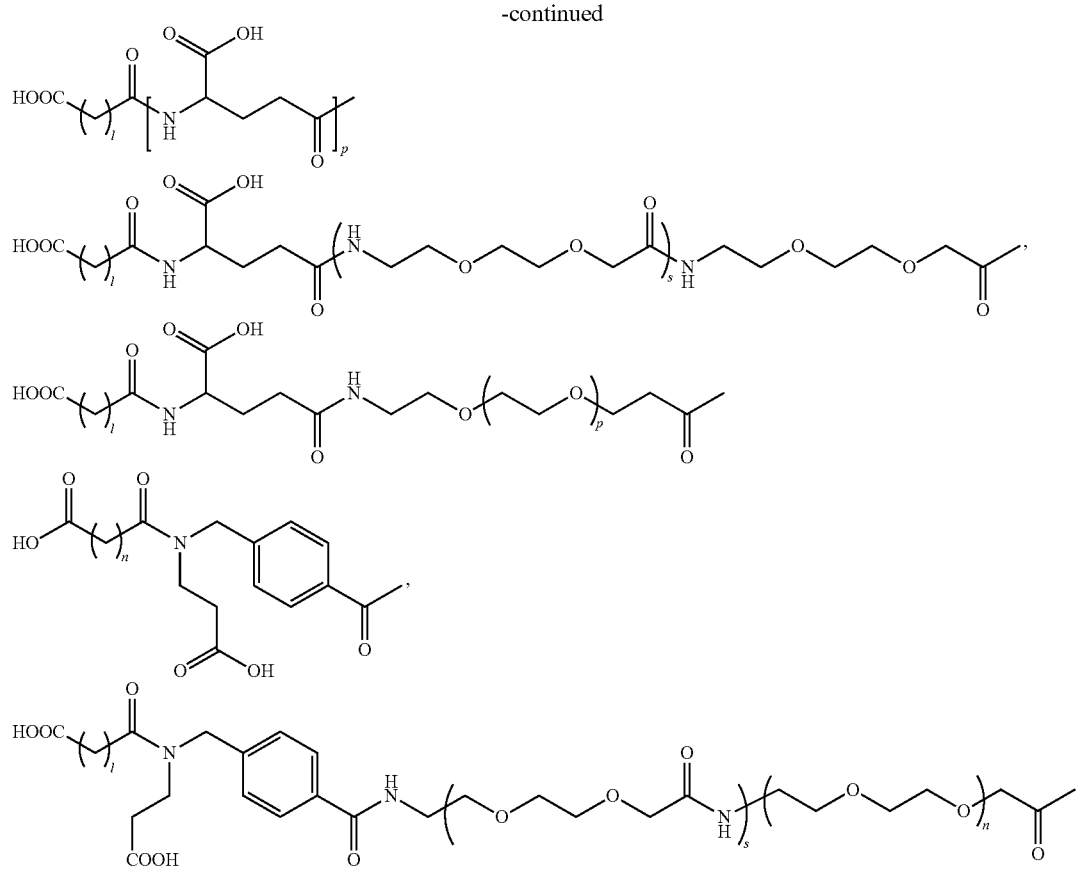

where l is 14, 15, 16, 17, 18, 19 or 20;
p is 1, 2, 3, or 4.
s is 0, 1 or 2
n is 0, 1 or 2

An embodiment according to any of the above embodiments is wherein B is

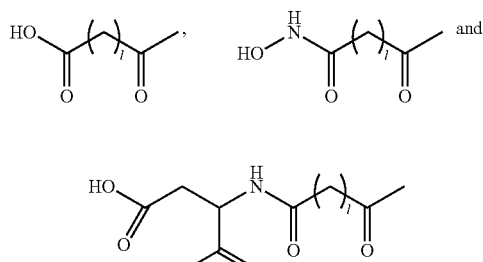

and l is 14, 16, 18 or 20;

An embodiment provides a GLP-1 analog according to any of the embodiments above, wherein B is

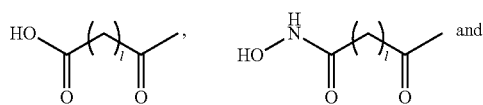

where l is 14, 15, or 16.

An embodiment provides a GLP-1 analog according to any of the embodiments above, wherein s is 1.

An embodiment provides a GLP-1 analog according to any of the embodiments above, wherein n is 1.

An embodiment provides a GLP-1 analog according any of the embodiments above, wherein l is 14, 15 or 16; In embodiments l is 17, 18, 19 or 20. In embodiments l is 15, 16 or 17. In embodiments l is 18, 19 or 20. In embodiments l is 14. In embodiments l is 16. In embodiments l is 18. In embodiments l is 20.

An embodiment provides a GLP-1 analog according to any of the embodiments above, wherein p is 1.

An embodiment provides a GLP-1 analog according to any of the embodiments above, wherein p is 2.

An embodiment provides a GLP-1 analog according to any of the embodiments above, wherein p is 3.

An embodiment provides a GLP-1 analog according to any of the embodiments above, wherein p is 4.

An embodiment provides a GLP-1 analog according to any of the embodiments above, wherein B—U' is

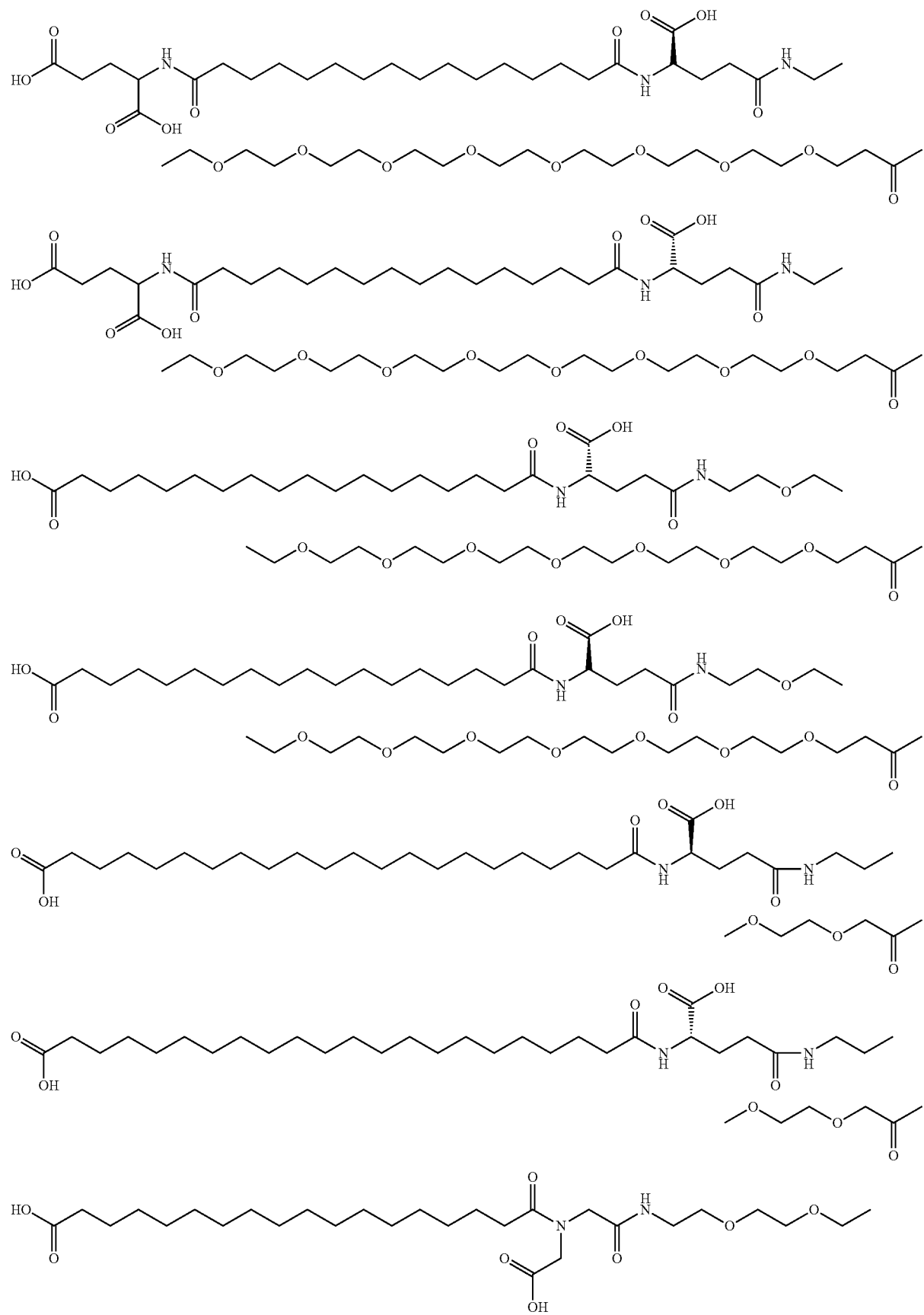

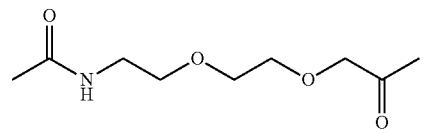

An embodiment provides a GLP-1 analog according to any of the embodiments above, wherein B—U' is

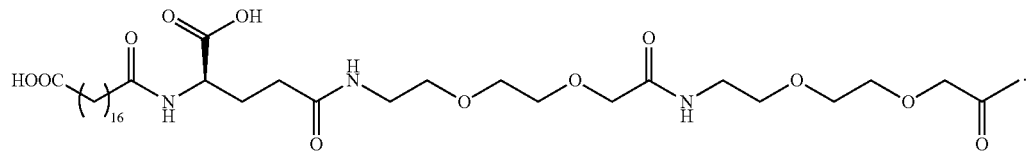

An embodiment provides a GLP-1 analog according to any of the embodiments above, wherein B—U' is

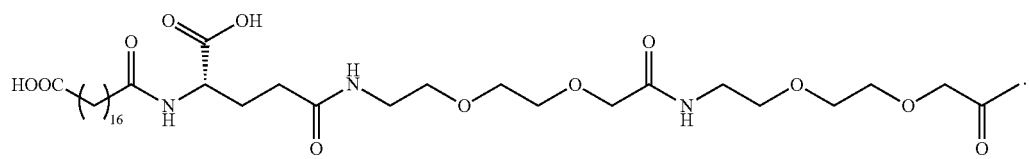

In another embodiment of the invention formula I or formula II is defined by
Xaa$_7$ is H is or desamino-histidine,
Xaa$_8$ is Ala, Gly, Val, Leu, Ile, Lys or Aib; Xaa$_{16}$ is Val; Xaa$_{18}$ is Ser; Xaa$_{19}$ is Tyr; Xaa$_{20}$ is Leu; Xaa$_{22}$ is Gly, Glu or Aib; Xaa$_{23}$ is Gln or Glu; Xaa$_{25}$ is Ala; Xaa$_{26}$ is Lys or Arg; Xaa$_{27}$ is Glu; Xaa$_{30}$ is Ala or Glu; Xaa$_{33}$ is Val; Xaa$_{34}$ is Lys or Arg; Xaa$_{35}$ is Gly or Aib; Xaa$_{36}$ is Arg, Lys, or is absent; Xaa$_{37}$ is Gly, Asn or is absent; Z is OH or NH$_2$ In another embodiment of the invention formula I or II is defined by
Xaa$_7$ is His; Xaa$_8$ is Aib; Xaa$_{16}$ is Val; Xaa$_{18}$ is Ser; Xaa$_{19}$ is Tyr; Xaa$_{20}$ is Leu; Xaa$_{22}$ is Gly; Xaa$_{23}$ is Gln; Xaa$_{25}$ is Ala; Xaa$_{26}$ is Arg; Xaa$_{27}$ is Glu; Xaa$_{30}$ is Ala; Xaa$_{33}$ is Val; Xaa$_{34}$ is Arg; Xaa$_{35}$ is Gly; Xaa$_{36}$ is Arg; Xaa$_{37}$ is Gly; Z is OH or NH$_2$;

In an embodiment of the invention
Xaa$_7$ is His; Xaa$_8$ is Aib; Xaa$_{16}$ is Val; Xaa$_{18}$ is Ser; Xaa$_{19}$ is Tyr; Xaa$_{20}$ is Leu; Xaa$_{22}$ is Gly; Xaa$_{23}$ is Gln; Xaa$_{25}$ is Ala; Xaa$_{26}$ is Arg; Xaa$_{27}$ is Glu; Xaa$_{30}$ is Ala; Xaa$_{33}$ is Val; Xaa$_{34}$ is Arg; Xaa$_{35}$ is Gly; Xaa$_{36}$ is Arg; Xaa$_{37}$ is Asn; Z is OH or NH$_2$;

An embodiment provides a GLP-1 analog according to any one of the above embodiments, wherein said GLP-1 analog comprises a modification of the N-terminal L-histidine in position 7 of the GLP-1(7-37) sequence.

An embodiment provides a GLP-1 analog according to the embodiment above, wherein said GLP-1 analog comprises imidazopropionyl[7], α-hydroxy-histidine[7] or N-methyl-histidine[7], D-histidine[7], desamino-histidine[7], 2-amino-histidine[7], β-hydroxy-histidine[7], homohistidine[7], N$^α$-acetyl-histidine[7], α-fluoromethyl-histidine[7], α-methyl-histidine[7], 3-pyridylalanine[7], 2-pyridylalanine[7] or 4-pyridylalanine[7].

An embodiment provides a GLP-1 analog according to any one of the above embodiments, wherein said GLP-1 analog comprises a substitution of the L-alanine in position 8 of the GLP-1(7-37) sequence for another amino acid residue.

An embodiment provides a GLP-1 analog according to the embodiment above, wherein said GLP-1 analog comprises Aib[8], Gly[8], Val[8], Ile[8], Leu[8], Ser[8], Thr[8], (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid.

An embodiment provides a GLP-1 analog according to any of the embodiment above, wherein said GLP-1 analog comprises Aib[8];

An embodiment provides a GLP-1 analog according to any of the above embodiments, wherein said GLP-1 analog comprises no more than fifteen amino acid residues which have been exchanged, added or deleted as compared to GLP-1(7-37) (SEQ ID No. 1), An embodiment provides a GLP-1 analog according to the embodiment above, wherein no more than ten amino acid residues which have been exchanged, added or deleted as compared to GLP-1(7-37) (SEQ ID No. 1).

An embodiment provides a GLP-1 analog according to the embodiment above, wherein said GLP-1 analog comprises no more than six amino acid residues which have been exchanged, added or deleted as compared to GLP-1 (7-37) (SEQ ID No. 1).

An embodiment provides a GLP-1 analog according to any of the above embodiments, wherein said GLP-1 analog comprises no more than 3 amino acid residues which are not encoded by the genetic code.

An embodiment provides a GLP-1 analog according to any of the above embodiments, wherein said GLP-1 analog comprises only one lysine residue.

An embodiment provides a GLP-1 analog according to any of the above embodiments, which is

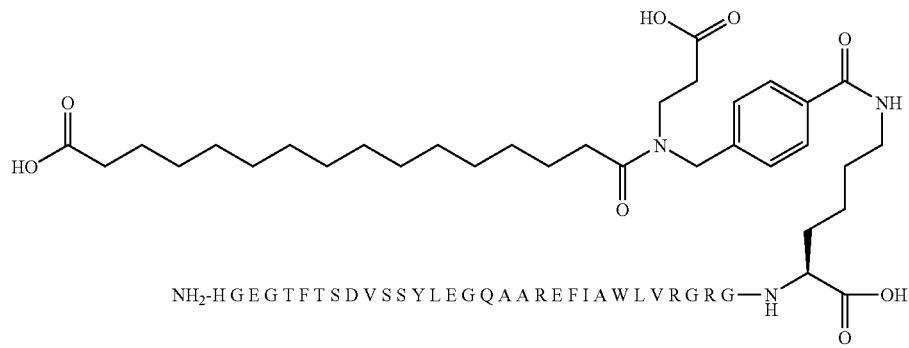
Lys$^{\epsilon 38}$((4-{[N-(2-carboxyethyl)-N-(15-carboxypentade-canoyl)amino]methyl}benzoyl) [Gly8; Arg26,34; Lys38] GLP-1-(7-37) peptide,
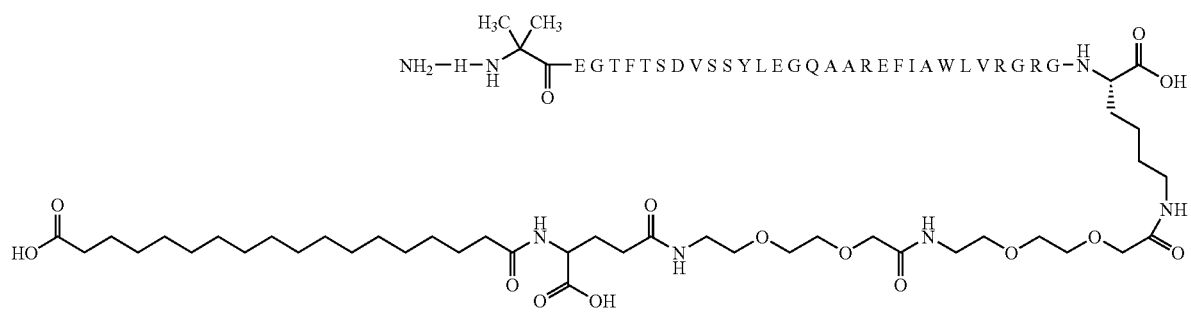
[Aib8,Arg26,34]GLP-1(7-37)Lys[2-(2-[2-(2-[2-(2-[4-(17-carboxyheptadecanoylamino)-4(S)-carboxybutyrylamino] ethoxy)ethoxy]acetylamino)ethoxy]ethoxy)acetyl]-OH,
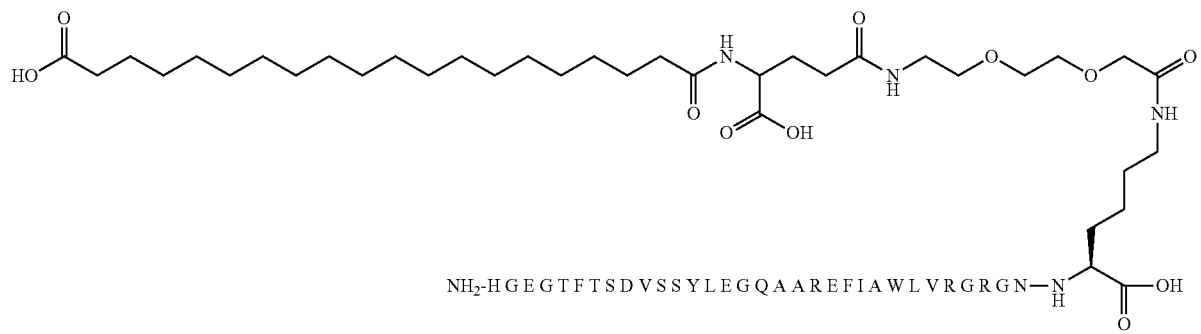

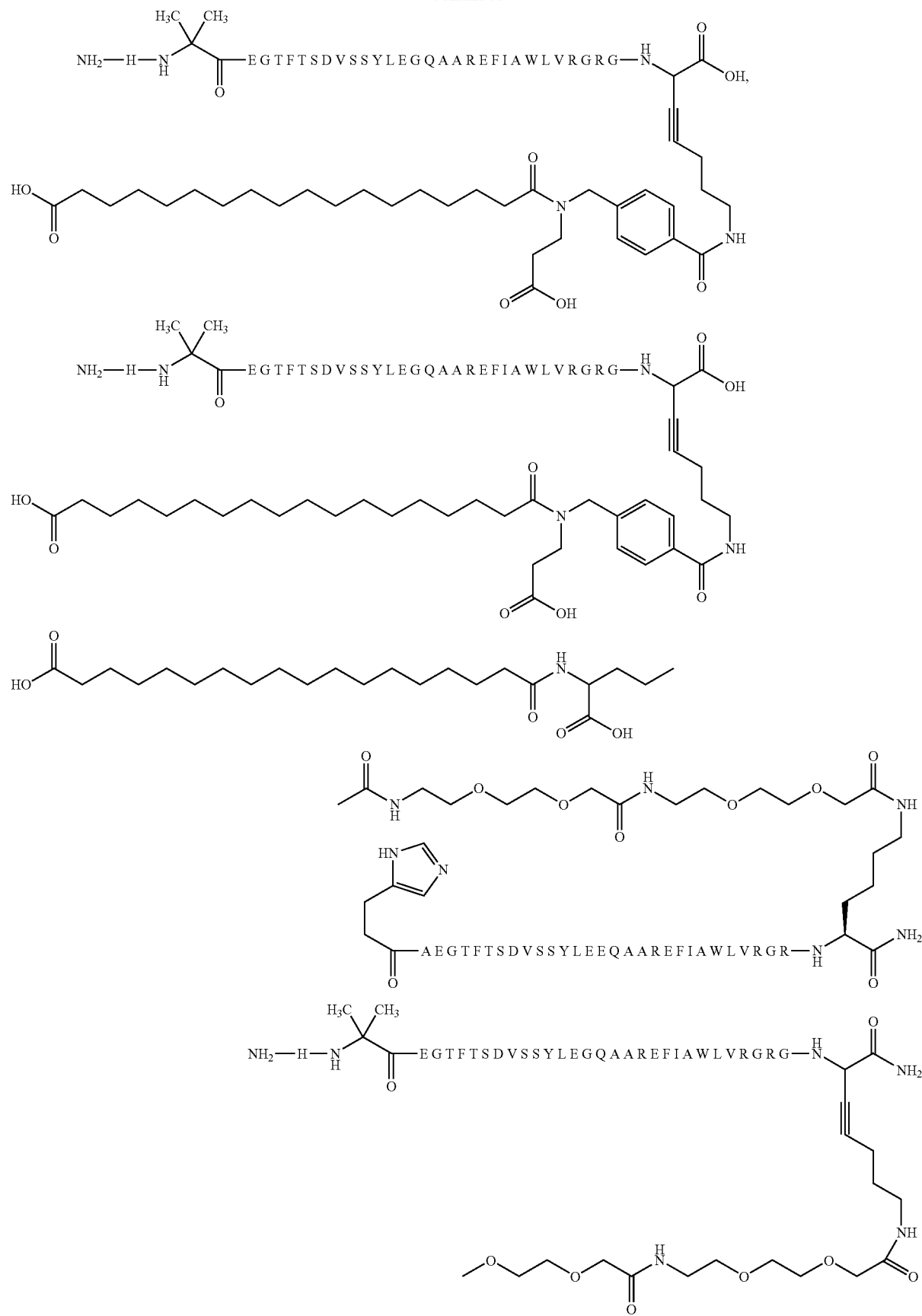

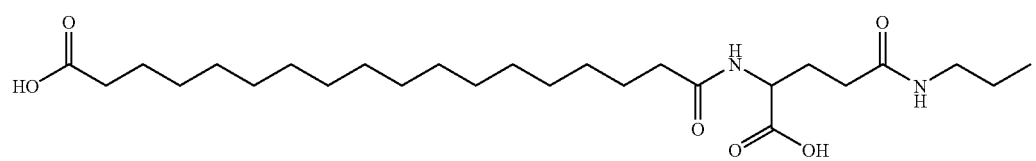
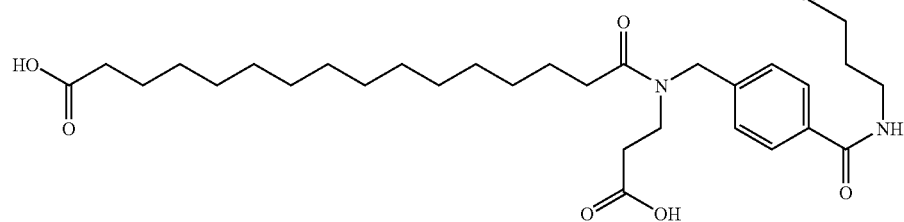
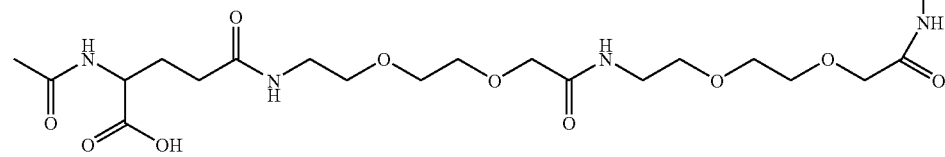
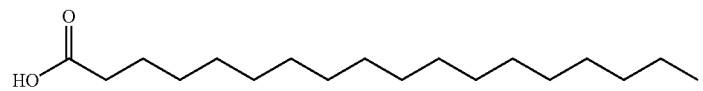
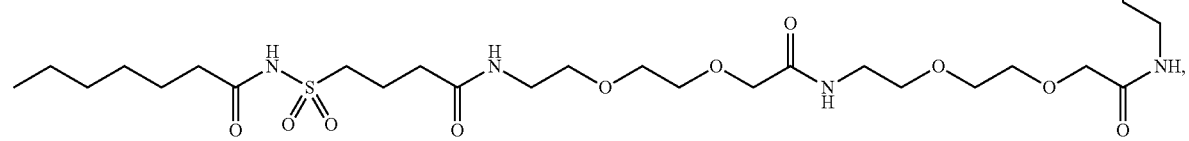
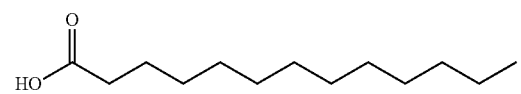

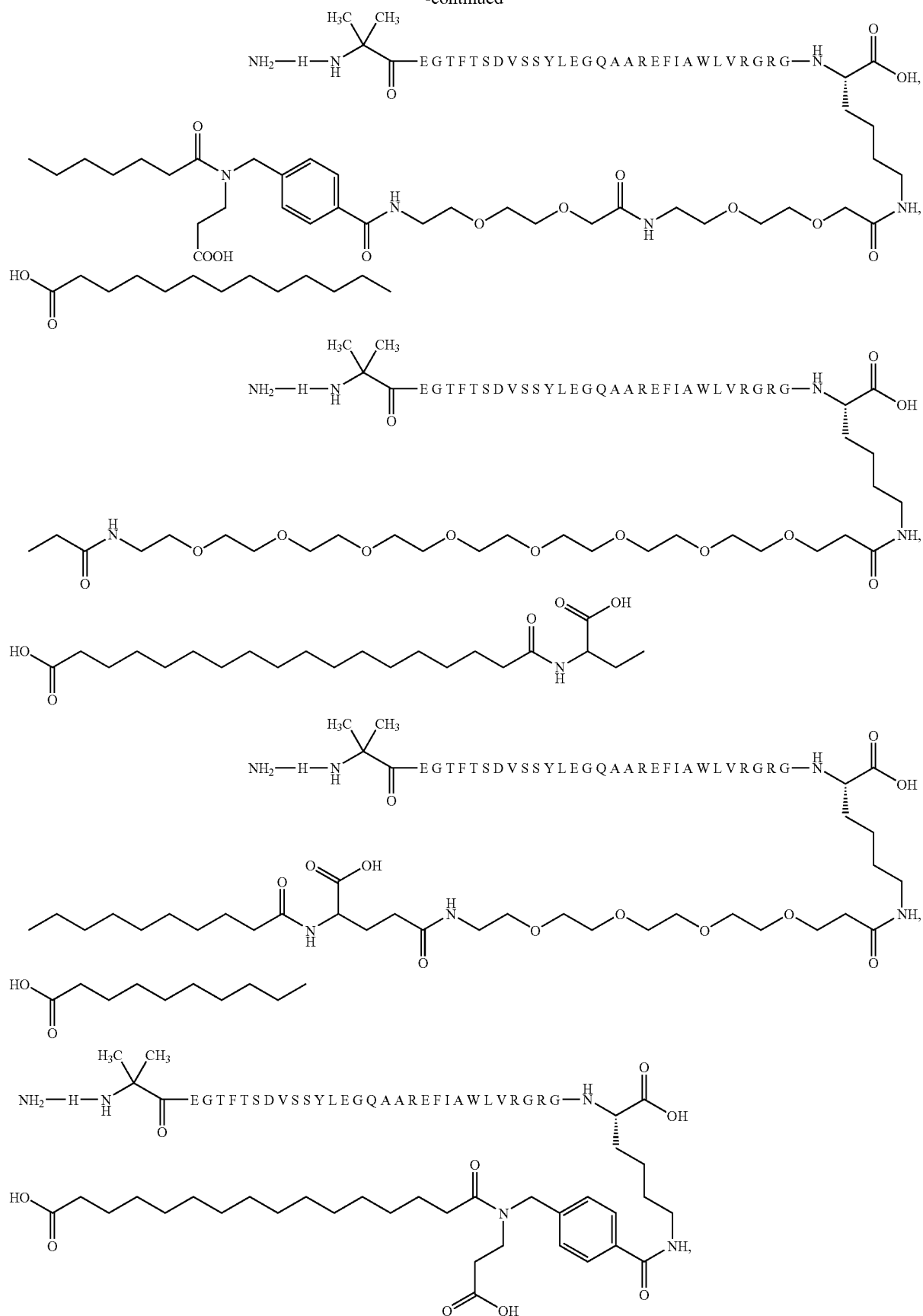

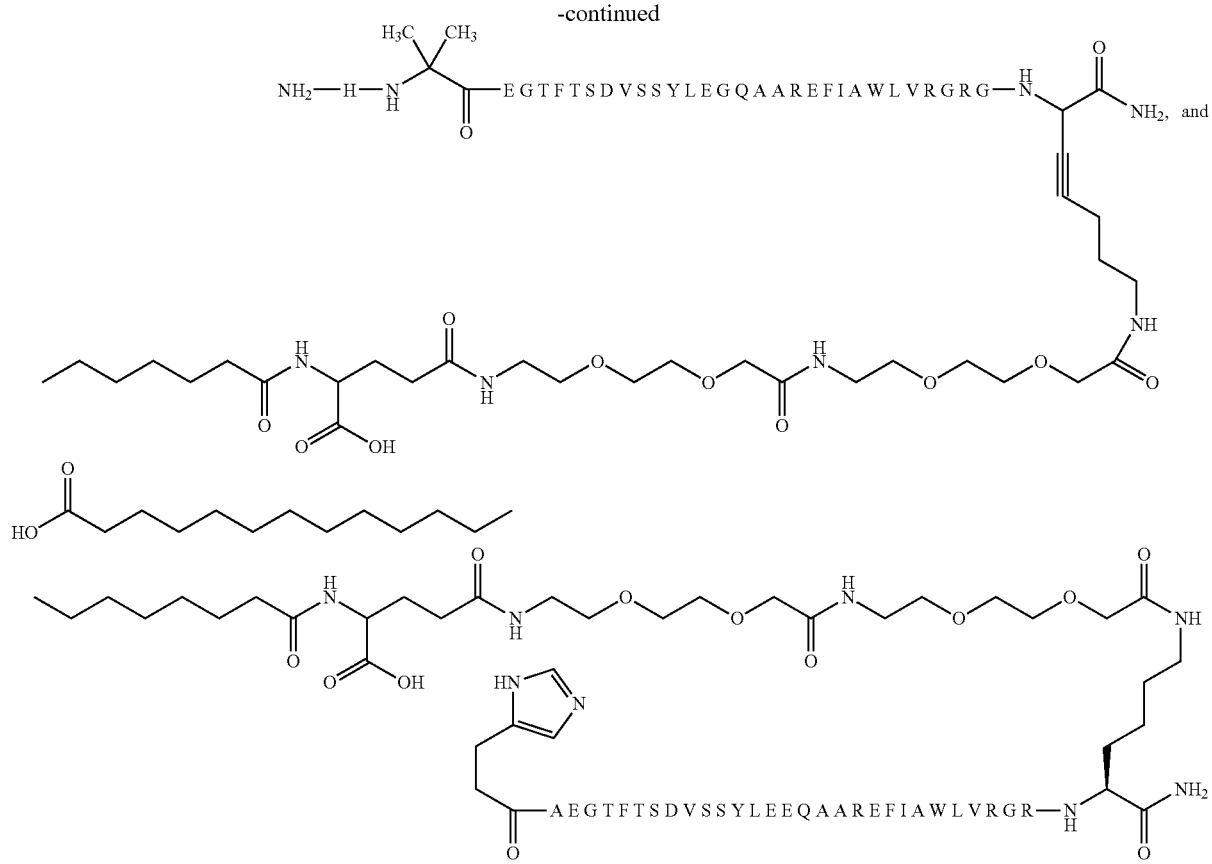

In another embodiment of the invention said diacid is a dicarboxylic acid.

In another embodiment of the invention the acylation group is a straight-chain or branched alkane α,ω-dicarboxylic acid.

In another embodiment of the invention the acylation group has the structure HOOC—(CH$_2$)$_n$CO—, wherein n is 12 to 20.

In another embodiment of the invention the acylation group has a structure selected from HOOC—(CH$_2$)$_{14}$CO—, HOOC—(CH$_2$)$_{15}$CO—, HOOC—(CH$_2$)$_{16}$CO—, HOOC—(CH$_2$)$_{17}$CO—, and HOOC—(CH$_2$)$_{18}$CO—.

In another embodiment of the invention the acylation group has the structure HOOC—(CH$_2$)$_{16}$CO—.

In another embodiment of the invention said GLP-1 analog comprises a modification of the N-terminal L-histidine in position 7 of the GLP-1(7-37) sequence. This modification confers increased stability against degradation by the DPPIV enzyme, e.g. a DPPIV stabilisation.

In another embodiment of the invention said GLP-1 analog comprises imidazopropionyl$^7$, α-hydroxy-histidine$^7$ or N-methyl-histidine$^7$.

In another embodiment of the invention said GLP-1 analog comprises D-histidine$^7$, desamino-histidine$^7$, 2-amino-histidine$^7$, β-hydroxy-histidine$^7$, homohistidine$^7$, N'-acetyl-histidine$^7$, α-fluoromethyl-histidine$^7$, α-methyl-histidine$^7$, 3-pyridylalanine$^7$, 2-pyridylalanine$^7$ or 4-pyridylalanine$^7$.

In another embodiment of the invention said GLP-1 analog comprises a substitution of the L-alanine in position 8 of the GLP-1(7-37) sequence for another amino acid residue.

In another embodiment of the invention said GLP-1 analog comprises Aib$^8$, Gly$^8$, Val$^8$, Ile$^8$, Leu$^8$, Ser$^8$ or Thr$^8$.

In another embodiment of the invention said GLP-1 analog comprises a substitution of the L-alanine in position 8 of GLP-1(7-37) sequence for (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid.

In another embodiment of the invention said GLP-1 analog comprises no more than fifteen amino acid residues which have been exchanged, added or deleted as compared to GLP-1(7-37) (SEQ ID No. 1), or no more than ten amino acid residues which have been exchanged, added or deleted as compared to GLP-1(7-37) (SEQ ID No. 1).

In yet another embodiment of the invention said GLP-1 analog comprises no more than six amino acid residues which have been exchanged, added or deleted as compared to GLP-1(7-37) (SEQ ID No. 1).

In another embodiment of the invention said GLP-1 analog comprises no more than 3 amino acid residues which are not encoded by the genetic code.

In another embodiment of the invention said GLP-1 analog comprises only one lysine residue.

In another aspect the present invention relates to a method for increasing the time of action in a patient of a GLP-1 analog, characterised in acylating said GLP-1 analog with a diacid on the lysine residue in position 37 or 38 of said GLP-1 analog.

In another aspect the present invention relates to a method for increasing the time of action in a patient of a GLP-1 analog to more than about 40 hours, characterised in modifying at least one of the amino acid residues in positions 7 and 8 of a GLP-1(7-37)Lys peptide or an analog thereof, and acylating the C-terminal amino acid Lys38 residue of the GLP-1 analog with a diacid via a hydrophillic spacer.

An embodiment provides a pharmaceutical composition comprising a compound according to any one the embodiments above, and a pharmaceutically acceptable excipient.

An embodiment provides a pharmaceutical composition according to the embodiment above, which is suited for parenteral administration.

An embodiment provides the use of a compound according to any one of the embodiments above for the preparation of a medicament.

An embodiment provides the use of a compound according to any one of the embodiments above for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

An embodiment provides the use of a compound according to any one of the embodiments above for the preparation of a medicament for delaying or preventing disease progression in type 2 diabetes.

An embodiment provides the use of a compound according to any one of the embodiments above for the preparation of a medicament for decreasing food intake, decreasing β-cell apoptosis, increasing β-cell function and β-cell mass, and/or for restoring glucose sensitivity to β-cells.

Another object of the present invention is to provide a pharmaceutical formulation comprising a compound according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 3.0 to about 9.0.

In another embodiment of the invention the pH of the formulation is from about 7.0 to about 9.5. In another embodiment of the invention the pH of the formulation is from about 3.0 to about 7.0. In another embodiment of the invention the pH of the formulation is from about 5.0 to about 7.5. In another embodiment of the invention the pH of the formulation is from about 7.5 to about 9.0. In another embodiment of the invention the pH of the formulation is from about 7.5 to about 8.5. In another embodiment of the invention the pH of the formulation is from about 6.0 to about 7.5. In another embodiment of the invention the pH of the formulation is from about 6.0 to about 7.0. In another embodiment the pharmaceutical formulation is from 8.0 to 8.5.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In an embodiment the preservative is phenol or m-cresol. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol)polyethyleneglycol (e.g. PEG400), or mixtures thereof. In an embodiment the isotoncity agent is propyleneglycol. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In an embodiment of the invention the isotonic agent is present in a concentration from 5 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In another embodiment of the invention the pharmaceutical composition comprises two different surfactants. The term "Surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general.

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2-bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), Dodecylphosphocholine (FOS-Choline-12), Decylphosphocholine (FOS-Choline-10), Nonylphosphocholine (FOS-Choline-9), dipalmitoyl phosphatidic acid, sodium caprylate, and/or Ursodeoxycholic acid.

Cationic surfactants may be selected from the group of: Alkyltrimethylammonium bromide
Benzalkonium chloride, Benzalkonium chloride, Benzyldimethylhexadecylammonium chloride, Benzyldimethyltetradecylammonium chloride, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Hexadecyltrimethylammonium bromide, Hexadecyltrimethylammonium bromide, Polyoxyethylene(10)-N-tallow-1,3-diaminopropane, Thonzonium bromide, and/or Trimethyl (tetradecyl)ammonium bromide.

Nonionic surfactants may be selected from the group of: BigCHAP, Bis(polyethylene glycol bis[imidazoyl carbonyl]), block copolymers as polyethyleneoxide/polypropyleneoxide block copolymers such as poloxamers, poloxamer 188 and poloxamer 407, Brij®35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-beta-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165 solution, Triton® X-305 solution, Triton® X-405, Triton® X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, sphingophospholipids (sphingomyelin), and sphingoglycolipids (ceramides, gangliosides), phospholipids, and/or n-Undecyl β-D-glucopyranoside.

Zwitterionic surfactants may be selected from the group of: CHAPS, CHAPSO, 3-(Decyldimethylammonio)propanesulfonate inner salt, 3-(Dodecyldimethylammonio)-propanesulfonate inner salt, 3-(Dodecyldimethylammonio)propanesulfonate inner salt, 3-(N,N-Dimethylmyristylammonio) propanesulfonate, 3-(N,N-Dimethyloctadecylammonio)-propanesulfonate, 3-(N,N-Dimethyloctylammonio) propanesulfonate inner salt, 3-(N,N-Dimethylpalmitylammonio)propanesulfonate, N-alkyl-N,N-dimethylammonio-1-propanesulfonates, 3-cholamido-1-propyldimethylammonio-1-propanesulfonate,
Dodecylphosphocholine, myristoyl lysophosphatidylcholine, Zwittergent 3-12 (N-dodecyl-N,N-dimethyl-3-ammonio-1-propanesulfonate), Zwittergent 3-10 (3-(Decyldimethylammonio)-propanesulfonate inner salt), Zwittergent 3-08 (3-(Octyldimethylammonio)pro-panesulfonate), glycerophospholipids (lecithins, kephalins, phosphatidyl serine), glyceroglycolipids (galactopyranoside), alkyl, alkoxyl(alkyl ester), alkoxy(alkyl ether)- derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, lysophosphatidylserine and lysophosphatidylthreonine, acylcarnitines and derivatives, $N^{beta}$-acylated derivatives of lysine, arginine or histidine, or side-chain acylated derivatives of lysine or arginine, $N^{beta}$-acylated derivatives of dipeptides comprising any combination of lysine, arginine or histidine and a neutral or acidic amino acid, $N^{beta}$-acylated derivative of a tripeptide comprising any combination of a neutral amino acid and two charged amino acids, or the surfactant may be selected from the group of imidazoline derivatives, long-chain fatty acids and salts thereof $C_6$-$C_{12}$ (eg. oleic acid and caprylic acid), N-Hexadecyl-N,N-dimethyl-3-ammonio-1-propane-sulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), or mixtures thereof.

The term "alkyl-polyglucosides" as used herein in relates to an straight or branched $C_{5-20}$-alkyl, -alkenyl or -alkynyl chain which is substituted by one or more glucoside moieties such as maltoside, saccharide etc. Embodiments of these alkyl-polyglucosides include $C_{6-18}$-alkyl-polyglucosides. Specific embodiments of these alkyl-polyglucosides includes the even numbered carbon-chains such as $C_6$, $C_8$, $C_{10}$, $C_{12}$, $C_{14}$, $C_{16}$, $C_{18}$ and $C_{20}$ alkyl chain. Specific embodiments of the glucoside moieties include pyranoside, glucopyranoside, maltoside, maltotrioside and sucrose. In embodiments of the invention less than 6 glucosid moieties are attached to the alkyl group. In embodiments of the invention less than 5 glucosid moieties are attached to the alkyl group. In embodiments of the invention less than 4 glucosid moieties are attached to the alkyl group. In embodiments of the invention less than 3 glucosid moieties are attached to the alkyl group. In embodiments of the invention less than 2 glucosid moieties are attached to the alkyl group. Specific embodiments of alkyl-polyglucosides are alkyl glucosides such n-decyl β-D-glucopyranoside, decyl β-D-maltopyranoside, dodecyl β-D-glucopyranoside, n-dodecyl β-D-maltoside, n-dodecyl β-D-maltoside, n-dodecyl β-D-maltoside, tetradecyl β-D-glucopyranoside, decyl β-D-maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, sucrose monocaprate, sucrose monolaurate, sucrose monomyristate, and sucrose monopalmitate.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors such as EDTA (ethylenediamine tetraacetic acid) and benzamidine HCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of compounds of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000). Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension or a powder for the administration of the compound of the present invention in the form of a nasal or pulmonal liquid or powder spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The compounds of the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit. Rev Ther Drug Carr Sys 14 (4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

Modifications to this relationship occur for non-spherical particles (cf. Edwards D A, Ben-Jebria A, Langer R. Recent advances in pulmonary drug delivery using large, porous inhaled particles. J Appl Physiol 84 (2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84 (2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84 (2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84 (2) (1998) 379-385).

Deep lung deposition of the pulmonal formulations comprising the compound of the present invention may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound of the present invention is stable for more than 6 weeks of usage and for more than 3 years of storage.

In another embodiment of the invention the pharmaceutical formulation comprising the compound of the present invention is stable for more than 4 weeks of usage and for more than 3 years of storage.

In a further embodiment of the invention the pharmaceutical formulation comprising the compound of the present invention is stable for more than 4 weeks of usage and for more than two years of storage.

In an even further embodiment of the invention the pharmaceutical formulation comprising the compound of the present invention is stable for more than 2 weeks of usage and for more than two years of storage.

In another aspect the present invention relates to the use of a compound according to the invention for the preparation of a medicament.

In one embodiment a compound according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, stroke, coronary heart disease and other cardiovascular disorders, inflammatory bowel syndrome, dyspepsia and gastric ulcers.

In another embodiment a compound according to the invention is used for the preparation of a medicament for delaying or preventing disease progression in type 2 diabetes.

In another embodiment a compound according to the invention is used for the preparation of a medicament for decreasing food intake, decreasing β-cell apoptosis, increasing β-cell function and β-cell mass, and/or for restoring glucose sensitivity to β-cells.

The treatment with a compound according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonist, PYY2 agonists, PYY4 agonits, mixed PPY2/PYY4 agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a compound according to this invention may also be combined with surgery—a surgery that influence the glucose levels and/or lipid homeostasis such as gastric banding or gastric bypass.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

| Abbreviations used: | |
|---|---|
| r.t | Room temperature |
| DIEA | diisopropylethylamine |
| $H_2O$ | water |
| $CH_3CN$ | acetonitrile |
| DMF | NN dimethylformamide |
| HBTU | 2-(1H-Benzotriazol-1-yl-)-1,1,3,3 tetramethyluronium hexafluorophosphate |
| Fmoc | 9 H-fluoren-9-ylmethoxycarbonyl |
| Boc | tert butyloxycarbonyl |
| OtBu | tert butyl ester |
| tBu | tert butyl |
| Trt | triphenylmethyl |
| Pmc | 2,2,5,7,8-Pentamethyl-chroman-6-sulfonyl |
| Dde | 1-(4,4-Dimethyl-2,6-dioxocyclohexylidene)ethyl |
| ivDde | 1-(4,4-Dimethyl-2,6-dioxocyclohexylidene)-3-methylbutyl |
| Mtt | 4-methyltrityl |
| Mmt | 4-methoxytrityl |
| DCM | dichloromethane |
| TIS | triisopropylsilane) |
| TFA: | trifluoroacetic acid |
| $Et_2O$: | diethylether |
| NMP | 1-Methyl-pyrrolidin-2-one |
| DIPEA: | Diisopropylethylamine |
| HATU: | O-(7-azabenzotriazol-1-yl)-1,1,3,3-tetramethyluronium hexafluorophosphate |
| HOAt: | 1-Hydroxy-7-azabenzotriazole |
| HOBt: | 1-Hydroxybenzotriazole |
| DIC: | Diisopropylcarbodiimide |

A: Synthesis of Resin Bound Peptide.

The protected peptidyl resin was synthesized according to the Fmoc strategy on an Applied Biosystems 433 peptide synthesizer in 0.25 mmol or 1.0 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methyl pyrrolidone), and UV monitoring of the deprotection of the Fmoc protection group. The starting resin used for the synthesis of the GLP-1 peptide amides was Rink-Amide resin and either Wang or chlorotrityl resin was used for GLP-1 peptides with a carboxy C-terminal. The protected amino acid derivatives used were standard Fmoc-amino acids (supplied from e.g. Anaspec, or Novabiochem) supplied in preweighed cartridges suitable for the ABI433A synthesizer with the exception of unnatural aminoacids such as Fmoc-Aib-OH (Fmoc-aminoisobutyric acid). The N terminal amino acid was Boc protected at the alpha amino group (e.g. Boc-His(Boc)OH was used for peptides with His at the N-terminal). The epsilon amino group of lysine in position 37 or 38 was either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2002/2003 or newer version, or W. R. Sampson (1999), J. Pep. Sci. 5, 403.

Procedure for Removal of ivDde or Dde-Protection.

The resin (0.25 mmol) was placed in a manual shaker/filtration apparatus and treated with 2% hydrazine in N-methylpyrrolidone (20 ml, 2×12 min) to remove the Dde or ivDde group and wash with N-methylpyrrolidone (4×20 ml).

Procedure for Removal of Mtt or Mmt-Protection.

The resin (0.25 mmol) was placed in a manual shaker/filtration apparatus and treated with 2% TFA and 2-3% TIS in DCM (20 ml, 5-10 min repeated 6-12 times) to remove the Mtt or Mmt group and wash with DCM (2×20 ml), 10% MeOH and 5% DIPEA in DCM (2×20 ml) and N-methylpyrrolidone (4×20 ml).

Procedure for Attachment of Sidechains to Lysine Residue.

The albumin binding residue (B—U— sidechain of formula I) can be attached to the GLP-1 peptide either by acylation to resin bound peptide or acylation in solution to the unprotected peptide using standard acylating reagent such as but not limited to DIC, HOBt/DIC, HOAt/DIC, or HBTU.

Attachment to Resin Bound Peptide:

Route I

Activated (active ester or symmetric anhydride) albumin binding residue (B—U— sidechain of formula I) such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, dichloromethane, 2-propanol, methanol and diethyl ether.

Route II

The albumin binding residue (B—U— sidechain of formula I) was dissolved in N-methyl pyrrolidone/methylene chloride (1:1, 10 ml). The activating reagent such as hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropyethylamine (4 molar equivalents relative to resin) was added. The resin was shaken 2 to 24 hours at room temperature. The resin was washed with N-methylpyrrolidone (2×20 ml), N-methyl pyrrolidone/Methylene chloride (1:1) (2×20 ml) and methylene chloride (2×20 ml).

Route III

Activated (active ester or symmetric anhydride) albumin binding residue (B—U— sidechain of formula I) such as octadecanedioic acid mono-(2,5-dioxo-pyrrolidin-1-yl) ester (Ebashi et al. EP511600, 1-1.5 molar equivalents relative to the GLP-1 peptide was dissolved in acetonitrile (1 ml) or THF (1 ml) and added to a solution of the peptide in water (10-20 ml) together with 10 molar equivalents of DIPEA. In case of protecting groups on the albumin binding residue such as tert.-butyl, the reaction mixture was lyophilized O/N and the isolated crude peptide was dissolved in a mixture of trifluoroacetic acid, water and triisopropylsilane (90:5:5) and standing for 30 min, evaporated in vacuo and by preparative HPLC.

Procedure for Removal of Fmoc-Protection:

The resin (0.25 mmol) was placed in a filter flask in a manual shaking apparatus and treated with N-methylpyrrolidone/methylene chloride (1:1) (2×20 ml) and with N-methylpyrrolidone (1×20 ml), a solution of 20% piperidine in N-methylpyrrolidone (3×20 ml, 10 min each). The resin was washed with N-methyl pyrrolidone (2×20 ml), N-methylpyrrolidone/Methylene chloride (1:1) (2×20 ml) and methylene chloride (2×20 ml).

Procedure for Cleaving the Peptide Off the Resin:

The peptide was cleaved from the resin by stirring for 180 min at room temperature with a mixture of trifluoroacetic acid, water and triisopropylsilane (95:2.5:2.5 to 92:4:4). The cleavage mixture was filtered and the filtrate was concentrated to an oil by a stream of nitrogen. The crude peptide was precipitated from this oil with 45 ml diethyl ether and washed 1 to 3 times with 45 ml diethyl ether.

Purification:

The crude peptide was purified by semipreparative HPLC on a 20 mm×250 mm column packed with 5μ or 7 μC-18 silica. Depending on the peptide two one or two purification systems were used.

TFA: After drying the crude peptide was dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The peptide containing fractions were collected. The purified peptide was lyophilized after dilution of the eluate with water.

Ammonium sulphate: The column was equilibrated with 40% $CH_3CN$ in 0.05M $(NH_4)_2SO_4$, which was adjusted to pH 2.5 with concentrated $H_2SO_4$. After drying the crude peptide was dissolved in 5 ml 50% acetic acid $H_2O$ and diluted to 20 ml with $H_2O$ and injected on the column which then was eluted with a gradient of 40%-60% $CH_3CN$ in 0.05M $(NH_4)_2SO_4$, pH 2.5 at 10 ml/min during 50 min at 40° C. The peptide containing fractions were collected and diluted with 3 volumes of $H_2O$ and passed through a Sep-Pak® C18 cartridge (Waters part. #:51910) which has been equilibrated with 0.1% TFA. It was then eluted with 70% $CH_3CN$ containing 0.1% TFA and the purified peptide was isolated by lyophilisation after dilution of the eluate with water.

The final product obtained was characterised by analytical RP-HPLC (retention time) and by LCMS The RP-HPLC analysis was performed using UV detection at 214 nm and a Vydac 218TP54 4.6 mm×250 mm 5 μC-18 silica column (The Separations Group, Hesperia, USA) which was eluted at 1 ml/min at 42° C. Two different elution conditions were used:

A1: Equilibration of the column with in a buffer consisting of 0.1M $(NH_4)_2SO_4$, which was adjusted to pH 2.5 with concentrated $H_2SO_4$ and elution by a gradient of 0% to 60% $CH_3CN$ in the same buffer during 50 min.

B1: Equilibration of the column with 0.1% TFA/$H_2O$ and elution by a gradient of 0% $CH_3CN$/0.1% TFA/$H_2O$ to 60% $CH_3CN$/0.1% TFA/$H_2O$ during 50 min. Alternative the RP-HPLC analysis was performed using UV detection at 214 nm and a Symmetry 300, 3.6 mm×150 mm, 3.5% C-18 silica column (Waters) which was eluted at 1 ml/min at 42° C.

B4: Equilibration of the column with 0.05% TFA/$H_2O$ and elution by a gradient of 5% $CH_3CN$/0.05% TFA/$H_2O$ to 95% $CH_3CN$/0.05% TFA/$H_2O$ during 15 min.

The following instrumentation was used:

LCMS was performed on a setup consisting of Sciex API 100 Single quadropole mass spectrometer, Perkin Elmer Series 200 Quard pump, Perkin Elmer Series 200 autosampler, Applied Biosystems 785A UV detector, Sedex 75 evaporative light scattering detector The instrument control and data acquisition were done by the Sciex Sample control software running on a Windows 2000 computer.

The HPLC pump is connected to two eluent reservoirs containing:

A: 0.05% Trifluoro acetic acid in water

B: 0.05% Trifluoro acetic acid in acetonitrile

The analysis is performed at room temperature by injecting an appropriate volume of the sample (preferably 20 μl) onto the column which is eluted with a gradient of acetonitrile.

The HPLC conditions, detector settings and mass spectrometer settings used are giving in the following table.

Column: Waters Xterra MS C-18×3 mm id 5 μm

Gradient: 5%-90% acetonitrile linear during 7.5 min at 1.5 ml/min

Detection: 210 nm (analogue output from DAD)

ELS (analogue output from ELS), 40° C.

MS ionisation mode API-ES

Alternatively LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detector controlled by HP Chemstation software. The HPLC pump is connected to two eluent reservoirs containing:

A: 10 mM $NH_4OH$ in water

B: 10 mM $NH_4OH$ in 90% acetonitrile

The analysis was performed at 23° C. by injecting an appropriate volume of the sample (preferably 20 μl) onto the column which is eluted with a gradient of A and B.

The HPLC conditions, detector settings and mass spectrometer settings used are giving in the following table.

Column Waters Xterra MS C-18×3 mm id 5 m

Gradient 5%-100% acetonitrile linear during 6.5 min at 1.5 ml/min

Detection 210 nm (analogue output from DAD)

ELS (analogue output from ELS)

MS ionisation mode API-ES. Scan 100-1000 amu step 0.1 amu

Radioligand Binding to Plasma Membranes Expressing the Human GLP-1 Receptor

The binding assay was performed with purified plasma membranes containing the human GLP-1 receptor. The plasma membranes containing the receptors were purified from stably expressing BHK tk-ts 13 cells. The membranes were diluted in Assay Buffer (50 mM HEPES, 5 mM EGTA, 5 mM $MgCl_2$, 0.005% Tween 20, pH=7.4) to a final concentration of 0.2 mg/ml of protein and distributed to 96-well microtiter plates precoated with 0.3% PEI. Membranes in the presence of 0.05 nM [$^{125}$I]GLP-1, unlabelled ligands in increasing concentrations and different HSA concentrations (0.005%, 0.05%, and 2%) were incubated 2 hr at 30° C. After incubation, unbound ligands were separated from bound ligands by filtration through a vacuum-manifold followed by 2×100 μl washing with ice cold assay buffer. The filters were dried overnight at RT, punched out and quantified in a γ-counter.

Example 1

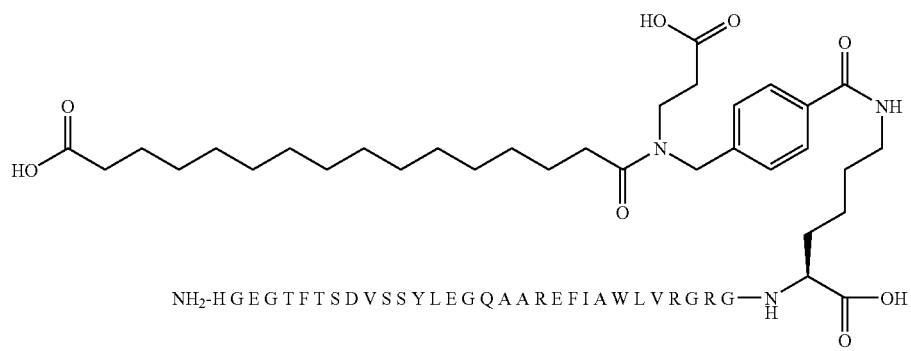

Lys$^{\varepsilon 38}$((4-{[N-(2-carboxyethyl)-N-(15-carboxypentadecanoyl)amino]methyl}benzoyl) [Gly8; Arg26,34; Lys38] GLP-1-(7-37) peptide

[Gly8; Arg26,34; Lys38]GLP-1-(7-37) peptide was prepared by standard Fmoc-solid phase peptide synthesis and purified by preparative HPLC. 4-{[N-(2-tert-Butoxycarbonylethyl)-N-(15-tertbutoxycarbonylpentadecanoyl)amino]methyl}benzoic acid (36 mg) was dissolved in THF (1.0 ml), and DIPEA (7 µl) and TSTU (17 mg) were added. After stirring at room temperature for 1 h the mixture was diluted with THF (1 ml). Of the resulting suspension, 200 µl was added to a solution of [Gly8; Arg26,34; Lys38]GLP-1-(7-37) peptide (15 mg) and DIPEA (15 µl) in water (1.0 ml). After 0.5 h more acylating agent (50 µl of the above solution) was added. After 1.5 h the mixture was concentrated under reduced pressure, and the tert-butyl esters solvolyzed by treatment with 95% TFA for 15 min. The final product was purified by preparative HPLC. 1.3 mg of the title compound was obtained.

HPLC (method B4): RT=9.13 min (93%)
LCMS: m/z=1334 (MH$_3^{3+}$). Calculated for (MH$_3^{3+}$): 1334

Example 2

[Aib8,Arg26,34]GLP-1(7-37)Lys[2-(2-[2-(2-[2-(2-[4-(17-carboxyheptadecanoylamino)-4(S)-carboxybutyrylamino]ethoxy)ethoxy]acetylamino)ethoxy]ethoxy)acetyl]-OH.

[Aib8; Arg26,34]GLP-1-(7-37)Lysine peptide was prepared by standard Fmoc-solid phase peptide synthesis and purified by preparative HPLC. [Aib8; Arg26,34]GLP-1-(7-37)Lysine was dissolved in water (10 ml) and DIPEA (37 ul) was added. 17-((S)-1-tert-Butoxycarbonyl-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl)heptadecanoic acid tert-butyl ester 4-[N-Hexadecanoylsulfamoyl]butyric acid (16 mg) was dissolved in acetonitrile (1 ml) and added in small portions. After stirring at room temperature for 40 min the reaction mixture was lyophilized O/N. To the isolated compound was added 10 ml of 90% TFA/5% TIS/5% water and the reaction mixture was standing for 30 min, evaporated in vacuo, and co-evaporated with heptane. The residual oil was dissolved in 15 ml of water containing 1% of NH$_3$-aq and purified by preparative HPLC to give the title compound.

HPLC (method B4): RT=9.25 min (100%)
LCMS: m/z=1423 (MH$_3^{3+}$). Calculated for (MH$_3^{3+}$): 1423

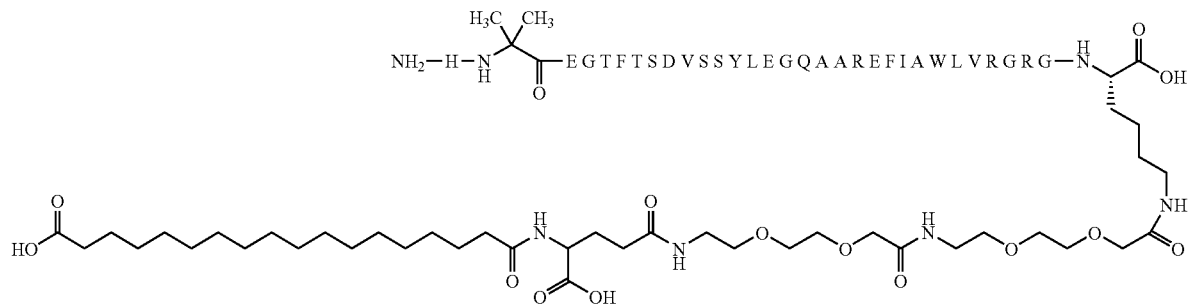

Example 3

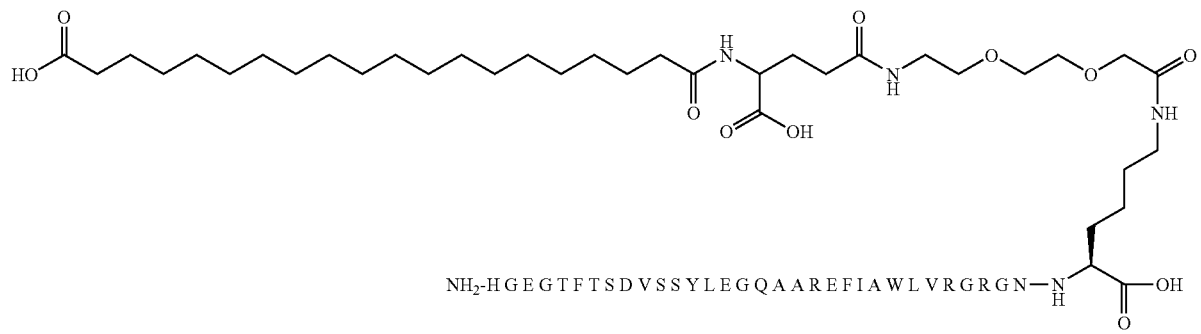

Example 4

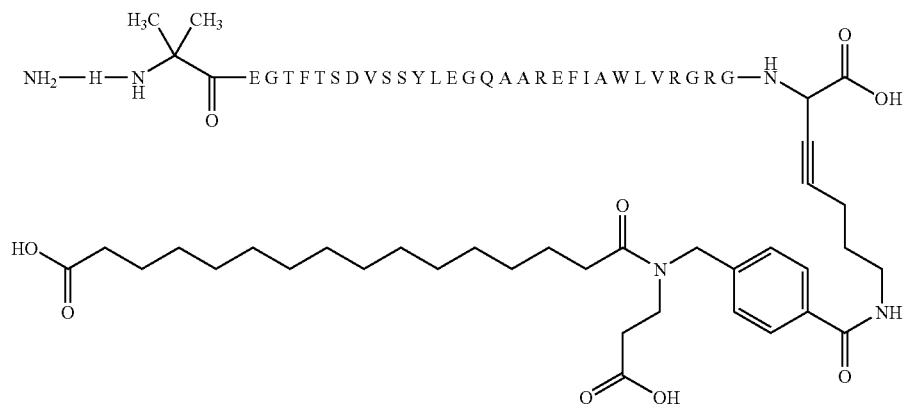

[Aib8,Arg26,34]GLP-1(7-37)Lys(4-{[N-(2-carboxyethyl)-N-(15-carboxypentadecanoyl)amino]methyl}benzoyl)-peptide

[Aib8,Arg26,34]GLP-1(7-37)Lys peptide starting from 150 mg 2-chlorotrityl chloride resin (1.4 mmol/g) was prepared by Fmoc-solid phase peptide synthesis using Apex396 from Advanced Chemtech. The Lys residue was protected as Lys(ivDde) while the functional side-chains for the other amino acids were protected with standard acid labile protecting groups. Then, 4-((N-(2-tert-butoxycarbonylethyl)-N-(15-tertbutoxycarbonylpentadecanoyl)amino)methyl)benzoic acid (126 mg) dissolved in NMP (1 ml) was coupled to the resin attached peptide using DIC/HOAt. The peptide was finally deprotected and cleaved from the resin with TFA/TIS/H₂O/thioanisol (90/5/3/2). The peptide was isolated by LC-MS.

HPLC: Elutes at 51.5% acetonitrile

MALDI-MS: 4025.

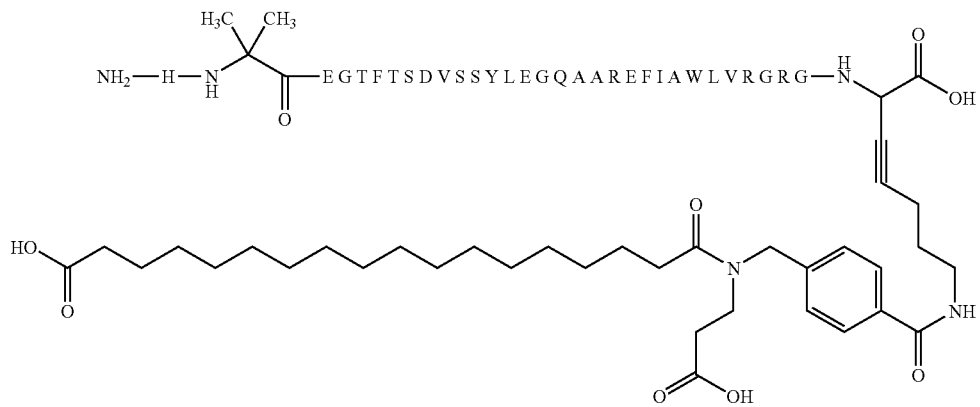

Example 5

[Aib8,Arg26,34]GLP-1(7-37)Lys(4-{[N-(2-carboxyethyl)-N-(17-carboxyheptadecanoyl)amino]methyl}benzoyl)-peptide

[Aib8,Arg26,34]GLP-1(7-37)Lys peptide starting from 150 mg 2-chlorotrityl chloride resin (1.4 mmol/g) was prepared by Fmoc-solid phase peptide synthesis using Apex396 from Advanced Chemtech. The Lys residue was protected as Lys(ivDde) while the functional side-chains for the other amino acids were protected with standard acid labile protecting groups. Then, 4-((N-(2-tert-butoxycarbonylethyl)-N-(17-tertbutoxycarbonylheptadecanoyl)amino)methyl)benzoic acid (126 mg) dissolved in NMP (1 ml) was coupled to the resin attached peptide using DIC/HOAt. The peptide was finally deprotected and cleaved from the resin with TFA/TIS/H$_2$O/thioanisol (90/5/3/2). The peptide was isolated by LC-MS.

HPLC: Elutes at 54.4% acetonitrile

MALDI-MS: 4057.

Example 6

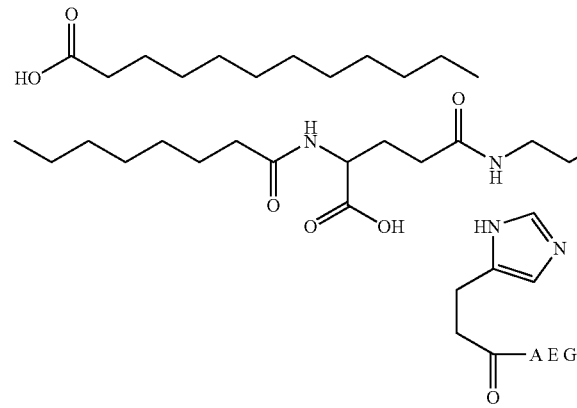

N-ε$^{37}$-[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl][ImPr$^7$,Glu$^{22}$,Arg$^{26,34}$, Lys$^{37}$], GLP-1-(7-37)peptide.

HPLC (method B6): RT=32.4 min
HPLC (method A1): RT=43.4 min
LCMS: m/z=1419.3 (MH$_3^{3+}$). Calculated for M$^+$: 4254.8

Example 7

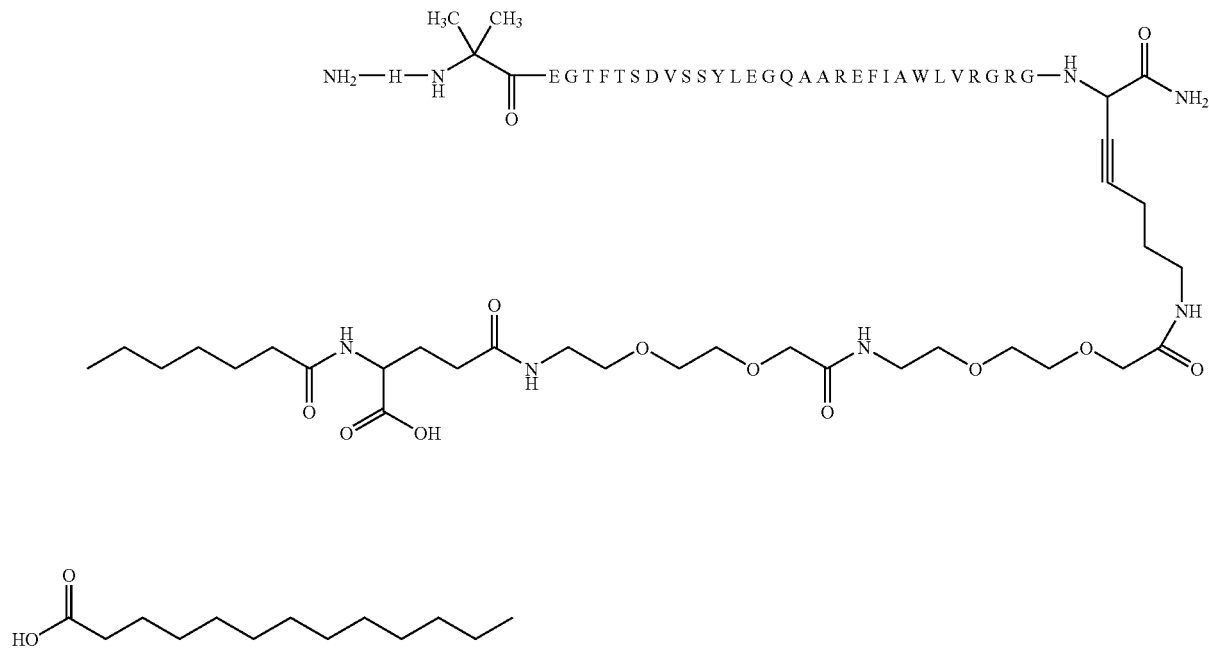

[Aib8,Arg26,34]GLP-1(7-37)Lys[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl]-amide

[Aib8,Arg26,34]GLP-1(7-37)Lys amide starting from 200 mg Tentagel RAM S resin (0.26 mmol/g) was prepared by Fmoc-solid phase peptide synthesis using Apex396 from Advanced Chemtech. The Lys residue was protected as Lys (ivDde) while the functional side-chains for the other amino acids were protected with standard acid labile protecting groups. The two units of OEG, Glu and octadecanedioic acid were coupled to the resin attached peptide using DIC/HOAt. The peptide was finally deprotected and cleaved from the resin with TFA/TIS/H₂O/thioanisol (90/5/3/2). The peptide was isolated by LC-MS.

HPLC: Elutes at 47% acetonitrile

MALDI-MS: 4267.

Example 8

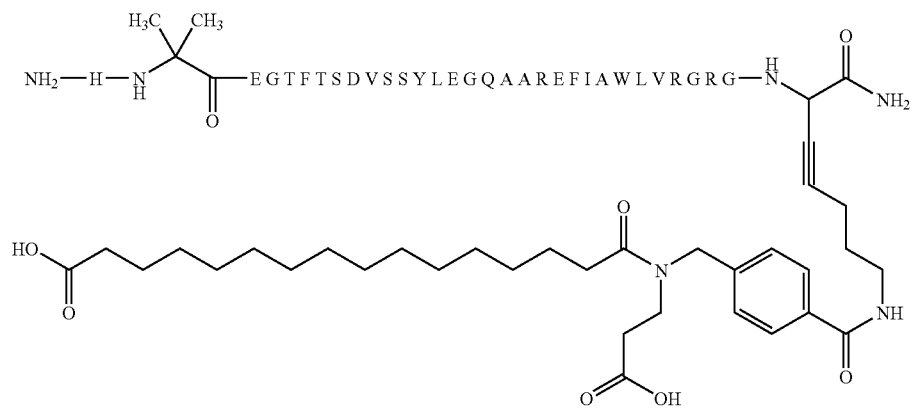

[Aib8,Arg26,34]GLP-1(7-37)Lys(4-{[N-(2-carboxyethyl)-N-(15-carboxypentadecanoyl)amino]methyl}benzoyl)-amide

[Aib8,Arg26,34]GLP-1(7-37)Lys amide starting from 200 mg Tentagel RAM S resin (0.26 mmol/g) was prepared by Fmoc-solid phase peptide synthesis using Apex396 from Advanced Chemtech. The Lys residue was protected as Lys (ivDde) while the functional side-chains for the other amino acids were protected with standard acid labile protecting groups. Then, 4-((N-(2-tert-butoxycarbonylethyl)-N-(15-ter-tbutoxycarbonylpentadecanoyl)amino)methyl)benzoic acid (119 mg) dissolved in NMP (1 ml) was coupled to the resin attached peptide by using DIC/HOAt. The peptide was finally deprotected and cleaved from the resin with TFA/TIS/H₂O/thioanisol (90/5/3/2). The peptide was isolated by preparative HPLC.

HPLC: Elutes at 51.5% acetonitrile

MALDI-MS: 4028

Example 9

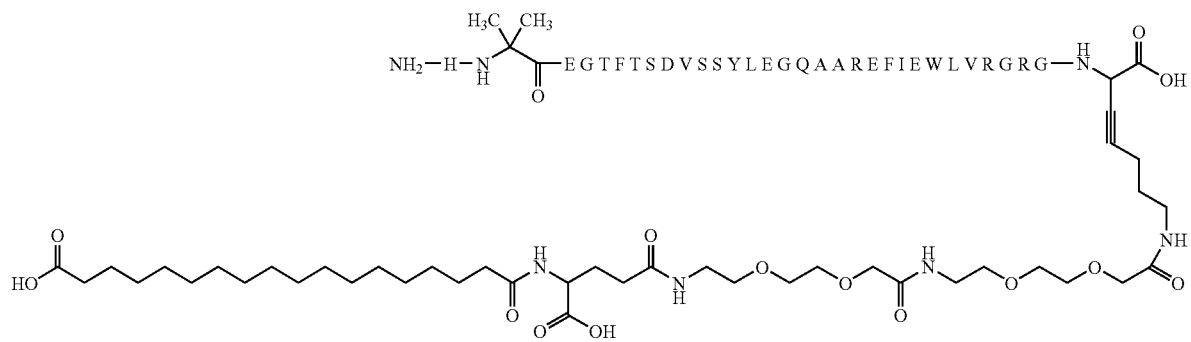

[Aib8,Arg26,34,Glu30]GLP-1(7-37)Lys[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl]-peptide

[Aib8,Arg26,34]GLP-1(7-37)Lys peptide starting from 150 mg 2-chlorotrityl chloride resin (1.4 mmol/g) was prepared by Fmoc-solid phase peptide synthesis using Apex396 from Advanced Chemtech. The Lys residue was protected as Lys (Mtt) while the functional side-chains for the other amino acids were protected with standard acid labile protecting groups. The two units of OEG, γGlu and monoprotected octadecanedioic acid were coupled to the resin attached peptide using DIC/HOAt. The peptide was finally deprotected and cleaved from the resin with TFA/TIS/H₂O/thioanisol (90/5/3/2). The peptide was isolated by preparative LC-MS.

HPLC: Elutes at 48.5% acetonitrile
MALDI-MS: 4328

Other compounds of this invention includes

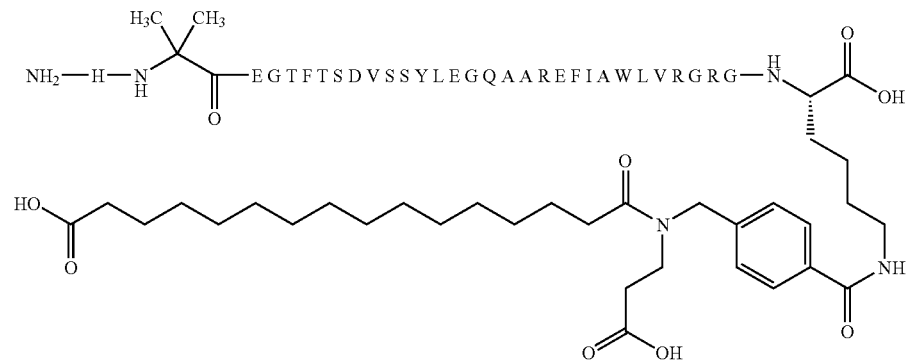

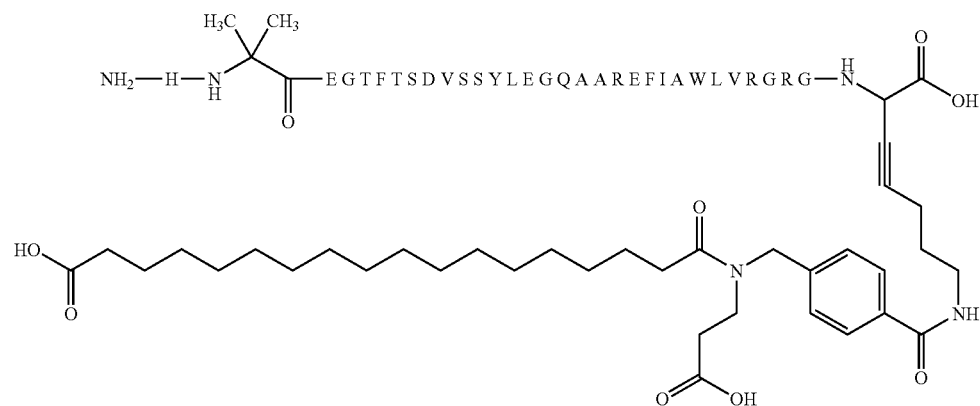

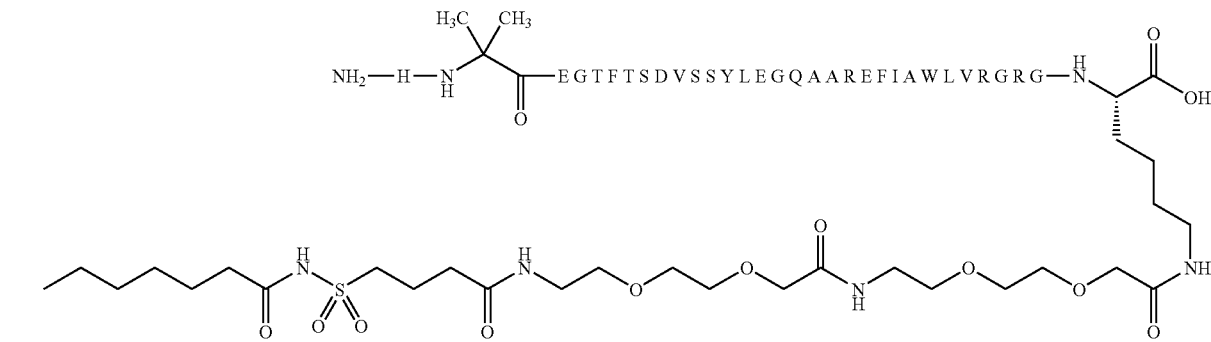

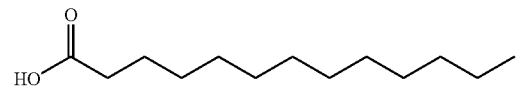

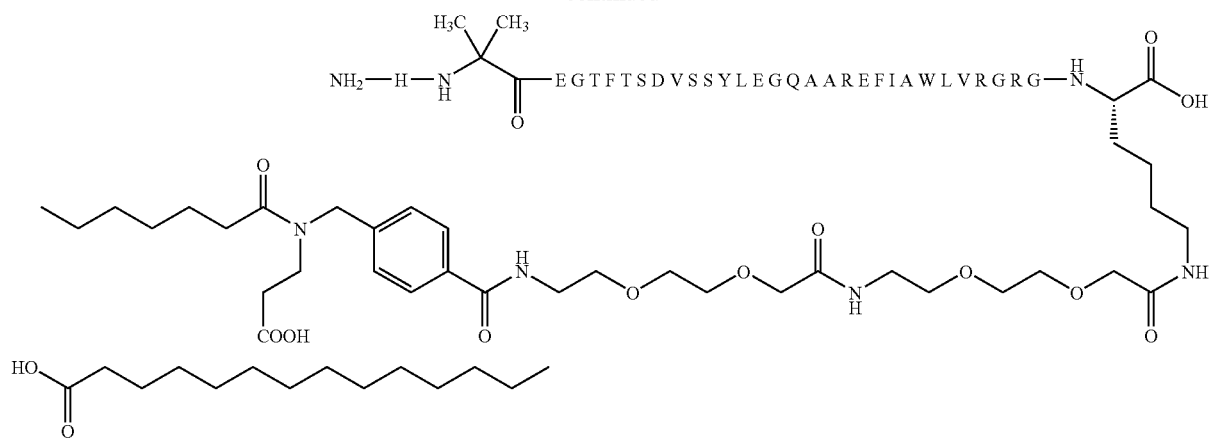
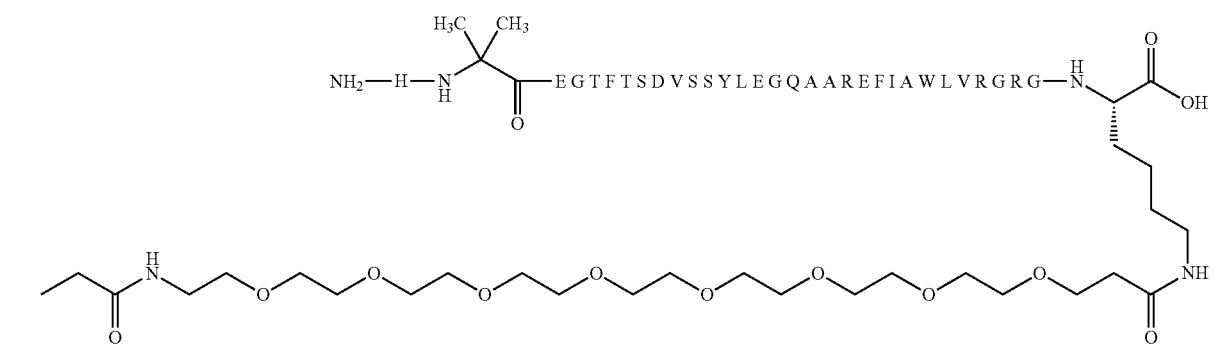
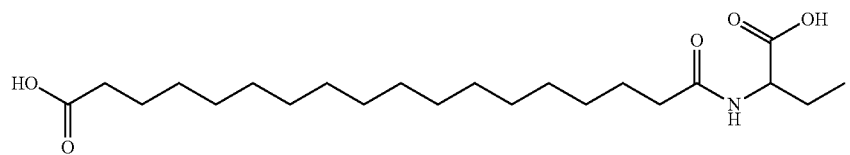
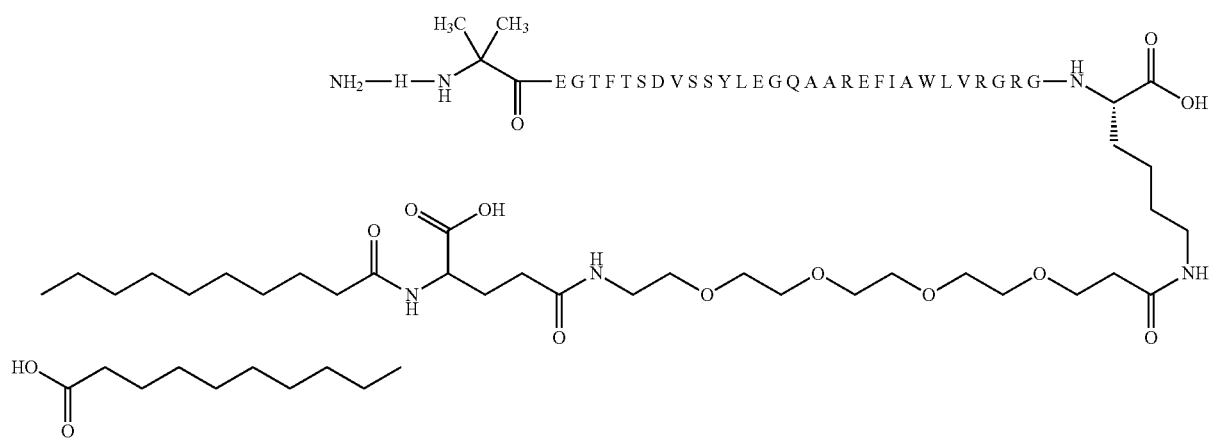

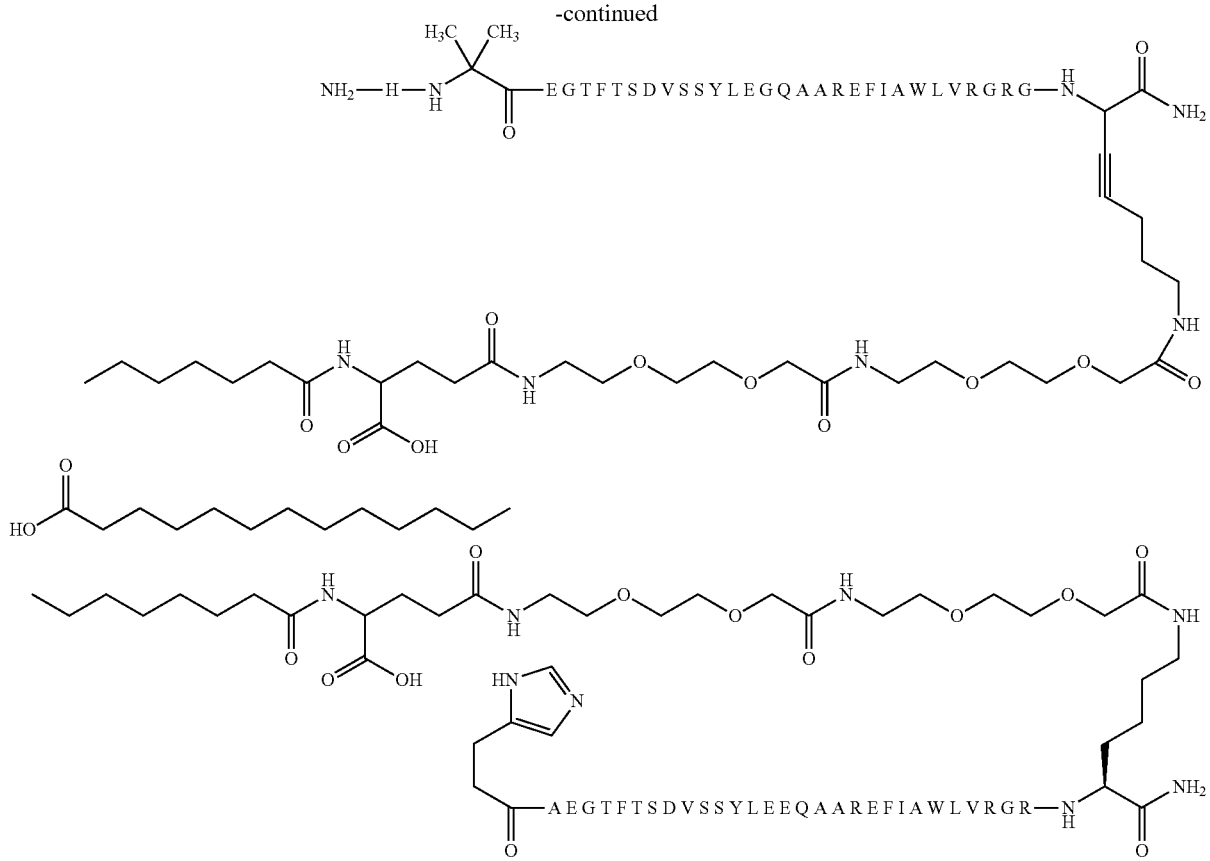

Pharmacodynamic Study Using db/db Mice

In one aspect of this invention the GLP-1 agonists have a duration of action of at least 24 hrs after dosing of 30 nmol/kg to db/db mice The efficacy and duration of action are measured in db/db mice.

Male db/db mice are shipped from Taconic, Denmark at the age of 8-10 weeks. From the time of arrival, the mice are housed under standard conditions but at 24° C. The mice are kept 10 per cage until experimentation with free access to standard chow (Altromin, Brogaarden APS., Denmark) and tap water at a normal day: light cycle (light on at 6 am). The mice are used for 1 experiment per week for 3 weeks. After this, the mice are euthanized.

After an acclimatisation period of 1 week, the blood glucose is measured by sampling from the tail tip capillary. In brief, 5 µl blood is sampled in heparinised glass capillary tubes and immediately suspended in 250 µl EBIO buffer solution (Eppendorf, Germany) in an 1.5 ml Eppendorf tube. The blood glucose concentration is measured by the glucose oxidase method at the EBIO Plus Auto analyser (Eppendorf, Germany).

The cut of value for blood glucose is 10 mM. When evaluating the mice, it is essential, that all 42 mice entering the experiment have blood glucose values above 10 mM, but also that the inter-mice variance is small. Therefore, if many mice are not severely diabetic, whereas some are, the start up of experiments should be postponed one week and new basal blood glucose measurements be made.

Based on the basal blood glucose values, the mice are allocated to 7 groups of n=6 with matching group mean blood glucose values.

On the day of testing the basal blood glucose morning values are assessed as described above and the basal body weight of each mouse is assessed. A time 0, the compound is dosed subcutaneously in the scruff of the neck (dosing volume app. 300 µl/50 g mouse).

The blood glucose values are followed up to 48 hours (time 1, 3, 6, 24 and 48 h) and the terminal body weight is assessed.

All data are entered into Graphpad Prism where mean blood glucose and mean delta body weights are calculated.

One aspect of this invention is to prepare GLP-1 analogues/derivatives with extended plasma half-lives that are suitable for once weekly administration. The pharmaco kinetic properties can be evaluated in mini pigs or domestic pigs as described below Pharmacokinetic Screening of Once Weekly GLP-1 Analogues Pharmacokinetic screening of GLP-1 analogues for identification of suitable once weekly candidates were performed on candidates that according to the project screenings plan were shown to be sufficiently potent with respect to glucose lowering potential in a diabetic mouse model (db/db mice) and subsequently had a time of duration of 48 hours or more in the db/db mouse model.

Primary Screening

The first part of the pharmacokinetic screening consisted of a single dose subcutaneous administration of 2 nmol/kg to three minipigs weighing 8-12 kg. Blood samples were drawn from each animal at predose, 0.5, 1, 2, 4, 6, 8, 12, 24, 48, 72, 96 and 120 hours post-injection. All blood samples were stabilised with a special stabilisation buffer consisting of: EDTA (di-sodium) 0.18 M, Aprotenin 15000 KIE/ml, Val-Pyr 0.30 mM, pH adjusted to 7.4 in order to prevent enzymatic degradation of the GLP-1 analogues. Plasma was collected from each stabilised blood samples by centrifugation (4° C., 10 min., 1270 G (4000 rpm), and analysed for the content of GLP-1 analogue by ELISA assays. Three different ELISA assays were used for the plasma analysis: "The "Total assay" using the antibody combination F1/Ra2135 detecting both the N-terminally intact 7-37GLP-1 molecule and the N-terminal enzymatically degraded 9-37GLP-1 molecule with a limit of detection (LOD) of 35 pM and a dynamic analytical range of 35-30000 pM. The "Intact assay" using the antibody combination F1/Mab26.1. This assay was detecting the N-terminally intact 7-37GLP-1 molecule only. The LOD was 35 pM and a dynamic analytical range of 35-30000 pM. The "Aib-intact assay" using the antibody combination F1/GLP162-3F15. This assay was detecting the Aib stabilised N-terminal of the GLP-1 molecule enabling detection of stabilised GLP-1 analogues. The LOD was 45 pM and the dynamic analytical range 45-30000 pM.

All plasma concentration-time profiles were analysed pharmacokinetically by a non-compartmental analysis. The following pharmacokinetic parameters were calculated if data permitted: $t_{max}$, $C_{max}$, AUC, AUC/Dose, $AUC_{\%Extrapol}$, $\lambda_z$, $t_{1/2}$, CL/F, $V_z$/F and MRT.

Secondary Screening

A second part of the pharmacokinetic screening was conducted on those compounds with an initial terminal half-life of 60-70 hours or more. This screening consisted of a single dose intravenous and subcutaneous administration of 2 nmol/kg to six minipigs for each route of administration. The blood sampling schedule was extended from 0-120 hours to 0-432 and 0-504 hours after intravenous and subcutaneous administration respectively. This was done in order to increase the precision and accuracy of the pharmacokinetic parameter estimates, especially the terminal half-life, AUC and the derived parameters clearance and volume of distribution, and to estimate the bioavailability after subcutaneous administration.

GLP-1 (Aib8-Intact) Assay

The assay was a two-site assay with simultaneous incubation of the analyte with catcher and detector antibody. A ready to use chemiluminescent substrate was used to maximize signal. The assay neither recognizes endogen GLP-1(7-37) nor the DPPIV cleaved GLP-1 (9-37).

Reference Plasma for GLP-1 Assays 0-plasma was prepared from pooled EDTA plasma without Valine Pyrrolidide and Aprotinin from fasting animals. The pooled EDTA plasma was incubated at 37° C. for 4 hours to remove traces of GLP-1 and after incubation Valine Pyrrolidide and Aprotinin were added.

Buffers
Coating Buffer
PBS was used as coating buffer: 10 mM sodium phosphate and 145 mM sodium chloride adjusted to pH 7.4.
Washing Buffer
PBS with 0.05% (v/v) Tween 20
Assay Buffer
PBS with 0.05% (v/v) Tween 20.10 g/L BSA and 10 mg/L anti-TNP.
Streptavidin Buffer
Washing buffer with an additional 0.5M NaCl.
Substrate
Ready to use substrate SuperSignal ELISA Femto (Pierce, cat. no. 37075).
Standards
Standards were prepared from a 25 µM stock solution of 0113-0000-0217. The peptide was serially diluted into reference plasma to make standards with final concentrations of 30000-10000-3333-1111-370-123-41 and 0 pM. Standards were stored in Micronic tubes in 100 µL aliquots at −20° C.
Assay Procedure
Crystal 2000 Microplates (black) were coated with monoclonal antibody GLPb1-7F1, 100 µL of 5 µg/mL in PBS overnight at 4° C.

Plates were washed 5 times with washing buffer in an automated plate washer (SkanWasher, Skatron) and allowed to stand for at least 30 min. with washing buffer to block remaining sites.

20 µL of sample or standard was added to each well in duplicate immediately followed by 100 µL GLP162-3F15 biotinylated, 1 µg/mL in assay buffer. Plates were incubated for 2 hours at room temperature on a plate shaker followed by 5 wash cycles as previously described. 100 µL of streptavidin-peroxidase solution (KPL, code 14-30-00, 1:20000 in streptavidin buffer) was added to each well and incubated for 1 hour at room temperature on a plate shaker. Plates were washed as previously described and after emptying 100 µL of SuperSignal femto was added. Plates were put on a shaker for 1 minute and measured in Orion Luminometer (Berthold). Data were transferred to MultiCalc and standard curves calculated using the weighted 4PL method. Sample concentrations were calculated from the standard curve.

GLP-1 (Total) Assay

The assay was a two-site assay with simultaneous incubation of the analyte with catcher and detector antibody. The assay recognizes N-terminally cleaved GLP-1 up to GLP-1 (12-37).

Buffers
Coating Buffer
PBS was used as coating buffer: 10 mM sodium phosphate and 145 mM sodium chloride adjusted to pH 7.4.
Washing Buffer
PBS with 0.05% (v/v) Tween 20
Assay Buffer
PBS with 0.05% (v/v) Tween 20.10 g/L BSA and 10 mg/L anti-TNP.
Streptavidin Buffer
Washing buffer with an additional 0.5M NaCl.
Substrate
Ready-to-use substrate TMB (KemEnTec code 4380A)
Stop Buffer
4 M $H_3PO_4$
Standards
Standards were prepared from a 25 µM stock solution of 0113-0000-0217. The peptide was serially diluted into reference plasma to make standards with final concentrations of 30000-10000-3333-1111-370-123-41 and 0 pM. Standards were stored in Micronic tubes in 100 µL aliquots at −20° C.
Assay Procedure
Maxisorp microtiter plates (NUNC) were coated with monoclonal antibody GLPb1-7F1, 100 µL of 5 µg/mL in PBS overnight at 4° C.

Plates were washed 5 times with washing buffer in an automated plate washer (SkanWasher, Skatron) and allowed to stand for at least 30 min. with washing buffer to block remaining sites.

20 µL of sample or standard was added to each well immediately followed by 100 µL Ra2135-biotinylated, 1 µg/mL in assay buffer. Plates were incubated for 2 hours at room temperature on a plate shaker followed by 5 wash cycles as previously described.

100 µL of streptavidin-peroxidase solution (Amersham Biosciences code RPN4401V, 1:8000 in assay buffer) was added to each well and incubated for 1 hour at room temperature on a plate shaker. Plates were washed as previously described and after emptying 100 µL of TMB was added and after 5 minutes stopped with 100 µL $H_3PO_4$.

Plates were measured in Victor Multilabel Reader (Wallac). Data were transferred to MultiCalc and standard curves calculated using the weighted 4PL method. Sample concentrations were calculated from the standard curve.

The in-life experimental procedures, plasma analysis and pharmacokinetic analysis were identical to that described under the primary screening.

The invention claimed is:

1. A glucagon-like peptide (GLP-1) analog having a modification of at least one non-proteogenic amino acid residue in positions 7 and/or 8 relative to the sequence GLP-1(7-37) (SEQ ID No 1), where said analog is acylated with a moiety to the lysine residue in position 37 or 38, and where said moiety comprises at least two acidic groups, wherein one acidic group is attached terminally, and wherein the GLP-1 analog is of formula I

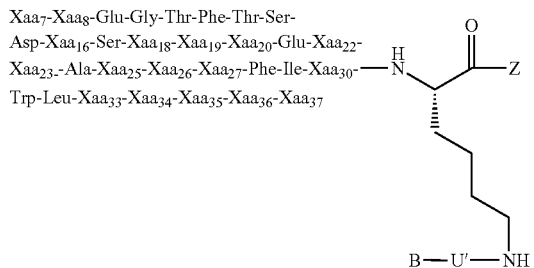

Formula I wherein

Xaa$_7$ is L-histidine, imidazopropionyl, α-hydroxy-histidine, D-histidine, desamino-histidine, 2-amino-histidine, β-hydroxy-histidine, homohistidine, Nα-acetyl-histidine, N$^α$-formyl-histidine, α-fluoromethyl-histidine, α-methyl-histidine, 3-pyridylalanine, 2-pyridylalanine or 4-pyridylalanine Xaa$_8$ is Ala, Gly, Val, Leu, Ile, Thr, Ser, Lys, Aib, (1-aminocyclopropyl)carboxylic acid, (1-aminocyclobutyl)carboxylic acid, (1-aminocyclopentyl)carboxylic acid, (1-aminocyclohexyl)carboxylic acid, (1-aminocycloheptyl)carboxylic acid, or (1-aminocyclooctyl)carboxylic acid;

Xaa$_{16}$ is Val or Leu;

Xaa$_{18}$ is Ser, Lys or Arg;

Xaa$_{19}$ is Tyr or Gln;

Xaa$_{20}$ is Leu or Met;

Xaa$_{22}$ is Gly, Glu or Aib;

Xaa$_{23}$ is Gln, Glu, Lys or Arg;

Xaa$_{25}$ is Ala or Val;

Xaa$_{26}$ is Lys, Glu or Arg;

Xaa$_{27}$ is Glu or Leu;

Xaa$_{30}$ is Ala, Glu or Arg;

Xaa$_{33}$ is Val or Lys;

Xaa$_{34}$ is Lys, Glu, Asn or Arg;

Xaa$_{35}$ is Gly or Aib;

Xaa$_{36}$ is Arg, Gly or Lys, or is absent;

Xaa$_{37}$ is Gly, Ala, Glu, Pro, Lys, Asn or is absent;

Z is OH or NH$_2$

B is an acidic group selected from

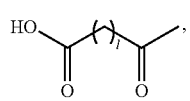

where l is 12, 13, 14, 15, 16, 17, 18, 19 or 20,

U' is a spacer selected from

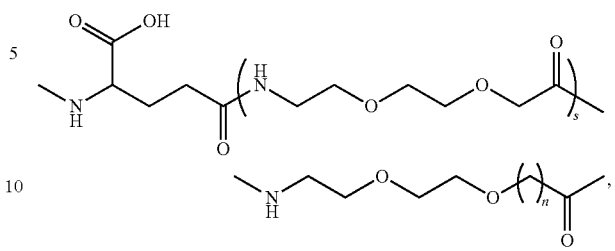

wherein n is 1, 2 or 3 and
s is 0, 1, 2, or 3.

2. A GLP-1 analog according to claim 1, wherein n is 1 or 2, s is 0, 1, or 2.

3. A GLP-1 analog according to claim 1, wherein l is 14, 15, 16, 17 or 18.

4. A GLP-1 analog according to claim 1, wherein s is 1.

5. A GLP-1 analog according to claim 1, wherein l is 16.

6. A GLP-1 analog according to claim 1, wherein n is 1.

7. A compound according to claim 1, where

Xaa$_7$ is His or desamino-histidine;
Xaa$_8$ is Ala, Gly, Val, Leu, Ile, Lys or Aib;
Xaa$_{16}$ is Val;
Xaa$_{18}$ is Ser;
Xaa$_{19}$ is Tyr;
Xaa$_{20}$ is Leu;
Xaa$_{22}$ is Gly, Glu or Aib;
Xaa$_{23}$ is Gln or Glu;
Xaa$_{25}$ is Ala;
Xaa$_{26}$ is Lys or Arg;
Xaa$_{27}$ is Glu;
Xaa$_{30}$ is Ala or Glu;
Xaa$_{33}$ is Val;
Xaa$_{34}$ is Lys or Arg;
Xaa$_{35}$ is Gly or Aib;
Xaa$_{36}$ is Arg, Lys, or is absent;
Xaa$_{37}$ is Gly, Asn or is absent;
Z is OH or NH$_2$.

8. A compound according to claim 7, where

Xaa$_7$ is His;
Xaa$_8$ is Aib;
Xaa$_{16}$ is Val;
Xaa$_{18}$ is Ser;
Xaa$_{19}$ is Tyr;
Xaa$_{20}$ is Leu;
Xaa$_{22}$ is Gly or Glu;
Xaa$_{23}$ is Gln;
Xaa$_{25}$ is Ala;
Xaa$_{26}$ is Arg;
Xaa$_{27}$ is Glu;
Xaa$_{30}$ is Ala;
Xaa$_{33}$ is Val;
Xaa$_{34}$ is Arg;
Xaa$_{35}$ is Gly;
Xaa$_{36}$ is Arg;
Xaa$_{37}$ is Gly or Asn;
Z is OH or NH$_2$.

9. A GLP-1 analog according to claim 1, wherein said GLP-1 analog comprises a modification of position 22 to a Glu.

10. A GLP-1 analog according to claim 1, wherein said GLP-1 analog comprises a modification of the N-terminal L-histidine in position 7 of the GLP-1(7-37) sequence.

11. A GLP-1 analog according to claim 10, wherein said GLP-1 analog comprises imidazopropionyl[7], α-hydroxy-histidine[7] or N-methyl-histidine[7], D-histidine[7], desamino-histidine[7], 2-amino-histidine[7], 13-hydroxy-histidine[7], homohistidine[7], N'-acetyl-histidine[7], α-fluoromethyl-histidine[7], α-methyl-histidine[7], 3-pyridylalanine[7], 2-pyridylalanine[7] or 4-pyridylalanine[7].

12. A GLP-1 analog according to claim 1, wherein said GLP-1 analog comprises a substitution of the L-alanine in position 8 of the GLP-1(7-37) sequence for another amino acid residue.

13. A GLP-1 analog according to claim 12, wherein said GLP-1 analog comprises Aib[8], Gly[8], Val[8], Ile[8], Leu[8], Ser[8], Thr[8], (1-aminocyclopropyl)carboxylic acid, (1-aminocyclobutyl)carboxylic acid, (1-aminocyclopentyl)carboxylic acid, (1-aminocyclohexyl)carboxylic acid, (1-aminocycloheptyl)carboxylic acid, or (1-aminocyclooctyl)carboxylic acid.

14. A GLP-1 analog according to claim 13, wherein said GLP-1 analog comprises Aib[8].

15. A GLP-1 analog according to claim 1, wherein said GLP-1 analog comprises no more than 3 amino acid residues which are not encoded by the genetic code.

16. A GLP-1 analog according to claim 1, wherein said GLP-1 analog comprises only one lysine residue.

17. A GLP-1 analog according to claim 1, wherein said Lysine is in position 38 relative to the sequence GLP-1(7-37) (SEQ ID No 1).

18. A compound according to claim 1, which is selected from

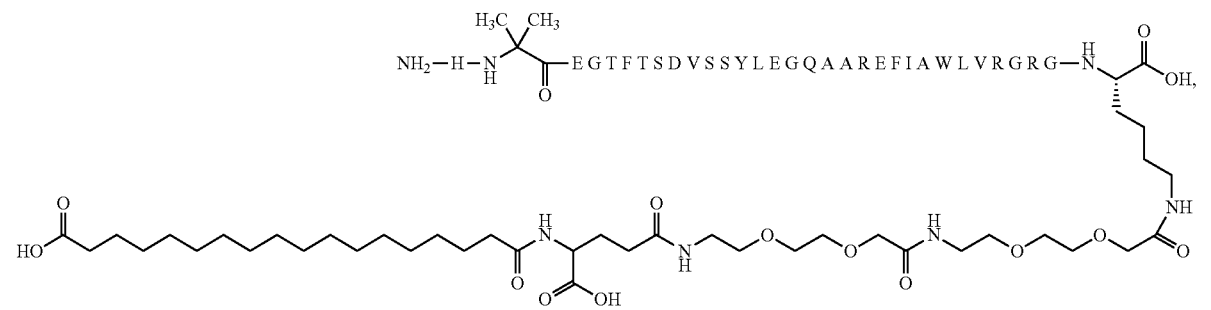

[Aib8,Arg26,34]GLP-1(7-37)Lys[2-(2-[2-(2-[2-(2-[4-(17-carboxyheptadecanoylamino)-4(S)-carboxybutyrylamino]ethoxy)ethoxy]acetylamino)ethoxy]ethoxy)acetyl]-OH,

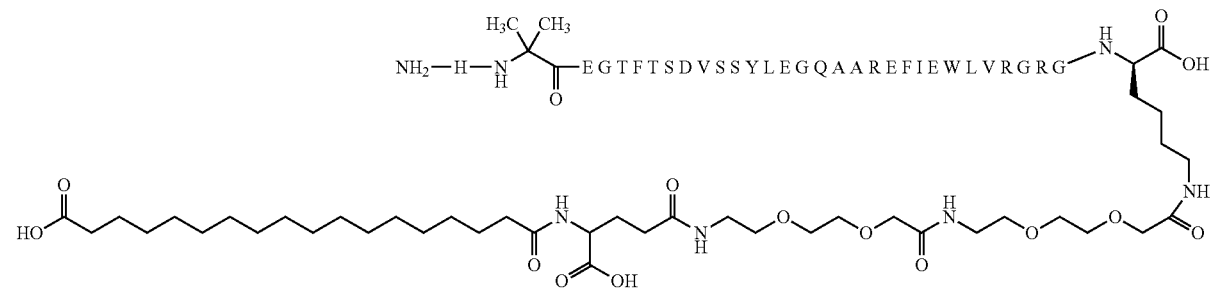

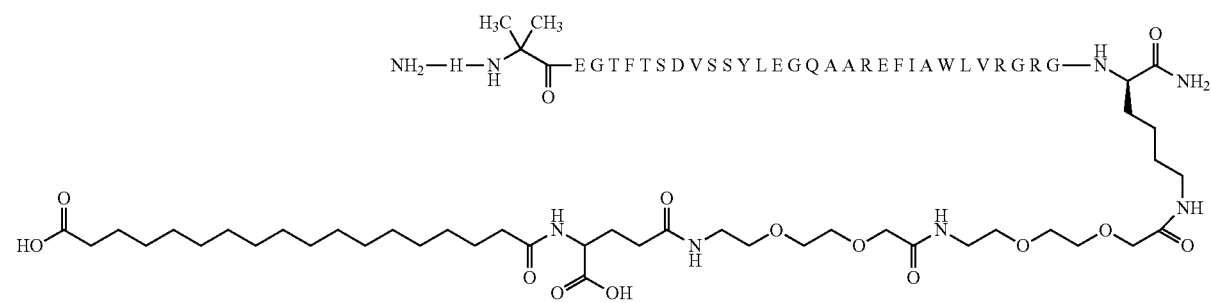

-continued

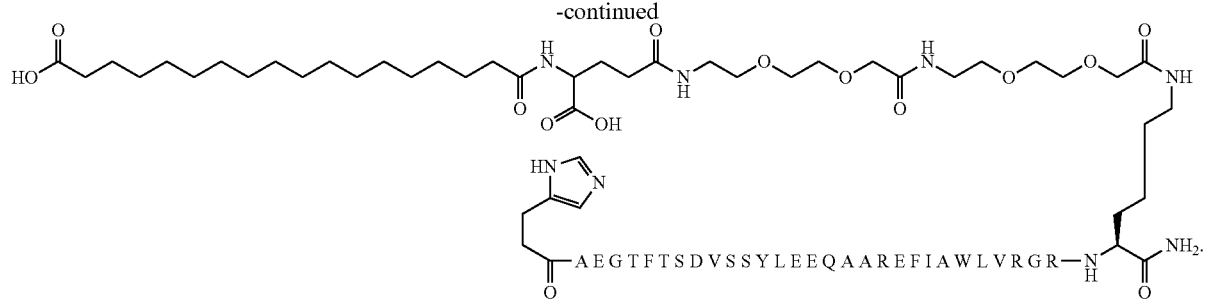

19. A method for increasing the time of action in a patient of a GLP-1 analog, said method comprising administering to a patient in need thereof said GLP-1 analog which has been acylated with a moiety B—U' as disclosed in claim 1, on the lysine residue in position 37 or 38 of said GLP-1 analog.

20. A method for increasing the time of action in a patient of a GLP-1 analog to more than about 40 hours, said method comprising administering to a patient in need thereof said GLP-1 analog where at least one of the amino acid residues in positions 7 and 8 of said GLP-1 analog thereof has been modified, and where acylating said GLP-1 analog has been acylated with a moiety B—U'—as disclosed in claim 1 on the lysine residue in position 37 or 38 of said GLP-1 analog.

21. A pharmaceutical composition comprising a compound according to claim 1, and a pharmaceutically acceptable excipient.

22. The pharmaceutical composition according to claim 21, which is suited for parenteral administration.

23. A method for treating hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and/or gastric ulcers in a subject, said method comprising administering to a subject in need of such treatment an effective amount of a GLP-1 analog according to claim 1.

24. A method for delaying disease progression in type 2 diabetes in a subject, said method comprising administering to a subject in need of such treatment an effective amount of a GLP-1 analog according to claim 1.

25. A method for decreasing food intake, decreasing β-cell apoptosis, increasing β-cell function and β-cell mass, and/or for restoring glucose sensitivity to β-cells in a subject, said method comprising administering to a subject in need of such treatment an effective amount of a GLP-1 analog according to claim 1.

* * * * *

UNITED STATES PATENT AND TRADEMARK OFFICE
CERTIFICATE OF CORRECTION

PATENT NO. : 8,603,972 B2  
APPLICATION NO. : 11/908836  
DATED : December 10, 2013  
INVENTOR(S) : Jesper Lau et al.

Page 1 of 1

It is certified that error appears in the above-identified patent and that said Letters Patent is hereby corrected as shown below:

In the Claims

At column 79, claim number 11, line number 4, please correct "13-hydroxy" to "B-hydroxy."

At column 80, claim number 18, line number 16, please including the following:

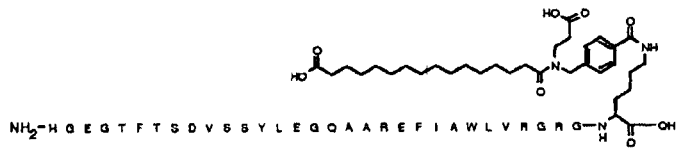

Lys$^{\varepsilon 38}$((4-{[N-(2-carboxyethyl)-N-(15-carboxypentadecanoyl)amino]methyl}benzoyl)[Gly8;Arg26,34;Lys38]GLP-1-(7-37) peptide, Signed and Sealed this  
Fourteenth Day of October, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,603,972 B2
APPLICATION NO. : 11/908836
DATED : December 10, 2013
INVENTOR(S) : Lau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1543 days.

Signed and Sealed this
Twenty-third Day of May, 2017

Michelle K. Lee
*Director of the United States Patent and Trademark Office*